United States Patent [19]

Jørgensen et al.

[11] Patent Number: 5,695,976
[45] Date of Patent: Dec. 9, 1997

[54] STABLE INTEGRATION OF DNA IN BACTERIAL GENOMES

[75] Inventors: Steen Troels Jørgensen, Allerød; Per Linå Jørgensen, Copenhagen; Børge Krag Diderichsen, Birkerød, all of Denmark

[73] Assignee: Novo Nordisk A/S, Bagsvaerd, Denmark

[21] Appl. No.: 441,714

[22] Filed: May 15, 1995

Related U.S. Application Data

[63] Continuation of Ser. No. 853,701, May 26, 1992, abandoned.

[30] Foreign Application Priority Data

Dec. 18, 1989 [DK] Denmark .................. 6396/89

[51] Int. Cl.$^6$ .................. C12N 15/64; C12N 15/65; C12N 15/75; C12P 21/02
[52] U.S. Cl. .................. 435/172.3; 435/69.1; 435/320.1
[58] Field of Search .................. 435/69.1, 252.35, 435/172.3, 320.1, 252.31

[56] References Cited

U.S. PATENT DOCUMENTS

| | | | |
|---|---|---|---|
| 4,401,761 | 8/1983 | Manis et al. | 435/172 |
| 4,631,257 | 12/1986 | Gelfand | 435/68 |
| 4,769,327 | 9/1988 | Stephens et al. | 435/69.8 |
| 4,959,316 | 9/1990 | Stanislas et al. | 435/172.3 |

FOREIGN PATENT DOCUMENTS

| | | |
|---|---|---|
| 0 127 328 | 12/1984 | European Pat. Off. . |
| WO 88/06623 | 9/1988 | WIPO . |

OTHER PUBLICATIONS

Seki et al., Genetics and Biotechnology of Bacilli., vol. 2, pp. 293–297, 1988.
Young et al., Journal of Bacteriology, vol. 171, No. 5, pp. 2653–2656, 1989.
Janniére et al., Mol. Gen Genet, vol. 210, pp. 116–121, 1987.
Ph. Noirot et al., J. Mol. Biol., vol. 196, pp. 39–48, 1987.
Villafane et al., Journal of Bacteriology, vol. 169, No. 10, pp. 4822–4829, 1987.
Dempsey et al., Journal of Bacteriology, vol. 171, No. 5, pp. 2866–2869, 1989.
Winnacker, E-L., From Genes to Clones: Introd. To Gene Technology, translation by Horst Ibelgaufts.—Weinheim; New York: VCH, p. 327, 1987.
Dubnau, D., CRC Critical Reviews in Biochemistry, vol. 16, Issue 2, pp. 103 and 107, 1984.
Gros et al., The EMBO Journal, vol. 6, No. 12, pp. 3863–3869 1987.
Errington Generalized Cloning Vectors for *Bacillus subtilis* in Rodriguez et al. ed. Vectors: A Survey of Molecular Cloning Vectors & Their Uses 1988 Butterworths, Boston 345, 357–359.
Noirot et al., J. Mol. Biol., vol. 196, pp. 39–48 (1987).
Gruss et al., Microbiological Reviews, vol. 53, No. 2, pp. 231–241 (1989).
Hofemeister et al., Mol. Gen. Genet., vol. 189, pp. 58–68 (1983).
Young et al., J. Bacteriology, vol. 171, No. 5, pp. 2653–2656 (1989).
Kallio et al., Appl. Microbiol. Biotechnol., vol. 27, pp. 64–71 (1987).

*Primary Examiner*—Nancy Degen
*Attorney, Agent, or Firm*—Steve T. Zelson; Cheryl H. Agris

[57] ABSTRACT

A bacterial cell which in its genome carries an integrated non-replicative DNA construct comprising (1) a DNA sequence of interest, (2) a DNA sequence which is homologous with a region of the genome of the cell, and (3) an origin of replication, the DNA construct lacking a functional gene coding for a factor required to initiate replication from the origin of replication.

49 Claims, 33 Drawing Sheets

↓ CULTIVATION → REPLICATION

CULTURED WITH KANAMYCIN

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 116 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
AATTGATCAA GCTTTAAATG CATGCTAGCA ACGCGGCCGC CAACCTCGAG ATCTCATGCT      60
```

```
AGTTCGAAAT TTACGTACGA TCGTTGCGCC GGCGGTTGGA GCTCTAGAGT ACTTAA                116
```

( 2 ) INFORMATION FOR SEQ ID NO:2:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

```
AATTCTGCAG ATATCAAGAT AAGAAAGAAC AAGTTCCG                                    38
```

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
GATCCGGAAC TTGTTCTTTC TTATCTTGAT ATCTGCAG                                    38
```

STABLE INTEGRATION OF DNA IN BACTERIAL GENOMES

This application is a continuation of application Ser. No. 07/853,701, filed May 26, 1992, now abandoned, the contents of which are incorporated herein by reference.

FIELD OF INVENTION

The present invention relates to a bacterial cell which comprises a DNA construct integrated in its genome, a DNA construct intended for integration in the genome of a bacterial cell, a plasmid vector comprising the DNA construct, and methods of integrating the DNA construct into bacterial genomes.

BACKGROUND OF THE INVENTION

When, for the purpose of producing a desired polypeptide by recombinant DNA procedures, bacterial cells are transformed with a recombinant plasmid vector which carries inserted genetic information coding for said polypeptide, it has often been observed that such plasmids become unstable even though they may, in themselves, be stably inherited in the cell. This instability may either take the form of unstable maintenance of the plasmid in the cells so that the plasmid will eventually be lost from a cell population, or so that the DNA coding for the protein in question may be deleted from the plasmid. A traditional way of solving the former problem has been to grow the transformed cells under selection pressure, that is, typically in the presence of an antibiotic to which the cells in question have been made resistant due to the presence of a gene coding for a product mediating resistance to that antibiotic on the plasmid transformed to the cells. This approach, however, is neither economically feasible in large-scale production due to the high cost of the antibiotics in question, nor is it desirable for environmental reasons. The use of antibiotics in culture media also makes it more difficult to obtain product approval from health authorities and the like.

It has previously been suggested to stabilise plasmids by inserting into them a DNA sequence encoding a partitioning function which ensures the even distribution of plasmids to progeny cells on cell division. An alternative method of achieving the stable inheritance of cloned DNA sequences is to provide for the integration of such DNA sequences in the genome of the host bacterium. Integration of DNA sequences present on plasmid vectors may take place by the so-called "crossing-over" procedure, e.g. as described by A. Campbell, *Advances Genet.* 11, 1962, pp. 101–145. According to this procedure, the plasmid vector is provided with a DNA sequence which is homologous to a region on the bacterial genome, or alternatively with two homologous sequences placed on either side of the heterologous DNA sequence to be integrated. In a subsequent recombination event, the homologous sequence and adjacent sequences on the vector are integrated into the host genome at the region of homology.

In some cases, however, is has been found that the integrated DNA sequences are deleted from the cells in the absence of selection pressure, for instance by a similar type of homologous recombination event as that responsible for the integration of the DNA. In particular, it has previously been observed that recombination between homologous DNA sequences is stimulated in the proximity of replicative DNA present on or near the DNA integrated in the host cell genome, cf. Ph. Noirot et al., *J. Mol. Biol.* 196, 1987, pp. 39–48; and M. Young and S. D. Ehrlich, *J. Bacteriol.* 171(5), May 1989, pp. 2653–2656.

An object of the present invention is therefore to provide stable integration of DNA sequences into genomic DNA, e.g. the chromosome, of bacterial host cells.

SUMMARY OF THE INVENTION

The present invention is based on the finding that stable integration of DNA sequences into the genome of host bacteria may be obtained by avoiding the presence of a functional plasmid replication system in the integrated DNA.

Accordingly, in one aspect, the present invention relates to a bacterial cell which in its genome carries an integrated non-replicative DNA construct comprising (1) a DNA sequence of interest, (2) a DNA sequence which is homologous with a region of the genome of the cell, and (3) an origin of replication, said DNA construct lacking a functional gene coding for a factor required to initiate replication from said origin of replication.

In another aspect, the present invention relates to a DNA construct comprising (1) a DNA sequence of interest, (2) a DNA sequence which is homologous with a region of the genome of a cell intended for introduction of the DNA construct, and (3) an origin of replication, said DNA construct lacking a functional gene coding for a factor required to initiate replication from said origin of replication.

In the present context, the term "non-replicative DNA construct" is intended to mean a DNA sequence which is unable to replicate autonomously and which is therefore replicated together with the host cell genome. The genome comprises the chromosome and stably inherited extrachromosomal elements. The term "DNA sequence of interest" is used to indicate a sequence which may code for a desired RNA or protein product (heterologous or native to the host cell) or which may in itself provide the host cell with a desired property, e.g. a mutant phenotype as described below.

The homologous DNA sequence may typically be one derived from the genome of the host cell, and may be homologous with a region of the genome which is not essential for the survival or proper functioning of the host cell. On the other hand, the homologous DNA sequence may also be so selected that integration of the DNA construct of the invention by homologous recombination will lead to a cell expressing a mutant phenotype (which may then serve as a marker for selection of cells in which the DNA construct has been integrated), for instance if the DNA construct is integrated within a transcription unit disrupting this so that one or more gene(s) contained within the transcription unit are consequently not expressed. The homologous DNA sequence may alternatively be one which is not native to the host genome but which has been cloned from another organism or which has been synthesized and subsequently introduced into the host genome by any convenient process, e.g. crossing-over, prior to the integration of the DNA construct of the invention. The homologous DNA sequence may be one which comprises or consists essentially of the DNA sequence of interest, whether native or foreign to the host cell in question (for instance native to the cell in cases where it is desired to amplify the copy number of the DNA sequence of interest in the cell, vide below). It should ba noted that, in the present context, the term "homologous" may be defined as a sequence identity of at least 9 consecutive base pairs.

DETAILED DISCLOSE OF THE INVENTION

Although, according to the invention, the stable integration of DNA into bacterial genomes has been demonstrated for plasmids with a particular type of replication system (the so-called rolling circle replication, vide below), it is currently expected that any plasmids which replicate by a mechanism where one or more trans-acting factors (i.e. RNA or protein factors) are required to initiate replication from cis-acting sequences on the plasmid (such cis-acting DNA sequences are collectively termed the origin of replication) will be useful for the present purpose. Factors which are necessary for plasmid replication will be termed replication factors in the following. When the DNA construct lacks a functional gene coding for a replication factor required by the origin of replication contained on said DNA construct, no active replication factor is produced and, consequently, no replication is initiated from the origin.

In order to obtain a DNA construct of the invention which lacks a functional gene encoding a required replication factor, one may either delete the entire gene or modify it in such a way that it encodes an inactive replication factor. Such modification of the gene may be carried out in a manner known per se by deletion, insertion or substitution of one or more nucleotides of the DNA sequence of the gene, or by similar modifications of transcriptional or translational start or stop signals.

The replication system outlined above may be utilised in a method of constructing a bacterial cell of the invention. In one embodiment of the method, a plasmid vector for the present purpose termed a parental vector, is initially constructed. The parental vector comprises (i) a first origin of replication; (ii) one or more functional genes encoding the replication factor(s) required for replication from said first origin of replication; (iii) a second origin of replication in the same orientation as the first origin of replication; (iv) a DNA sequence of interest, and (v) a DNA sequence which is homologous with a region of the genome of a cell intended for introduction of the vector, said parental vector lacking a functional gene encoding a replication factor required for replication from the second origin of replication in the region between the second and the first origin of replication (in the above-mentioned order). It should be noted that, in the present context, the term "plasmid" is also intended to denote a bacteriophage or other DNA molecule capable of functioning as an autonomously replicating extrachromosomal element.

According to the invention, this parental vector may then be transformed into bacterial cells, and the transformed cells are cultured under conditions permitting replication of the vector.

Replication of the parental vector in the transformed cell gives rise to the formation of two different progeny vectors.

The first progeny vector comprises (i) a first origin of replication; (ii) one or more genes encoding the replication factor(s) required for replication from said origin. The second progeny vector comprises (iii) a second origin of replication; (iv) a DNA sequence of interest, and a DNA sequence which is homologous with a region of the genome of a cell intended for introduction of the plasmid vector, said second progeny vector lacking a functional gene coding for a replication factor required for replication from the second origin of replication carried on said second progeny vector. The formation of two progeny vector molecules from the parent vector may take place by different mechanisms; either as a result of the mode of replication of the plasmid, for instance rolling circle replication of single-stranded DNA plasmids (vide below), or as a result of homologous recombination between the DNA regions including and/or adjacent to the two origins of replication present on the plasmid vector.

When the second origin is located in the same orientation on the parent plasmid as the first origin, the various DNA sequences intended to be integrated into the bacterial genome and located downstream of the second origin, but upstream of the first origin (i.e. the DNA sequence of interest, and the DNA sequence which is homologous with a region of the genome of the cell) will be present on the second progeny vector following plasmid replication. Continued culturing of the transformed cells may spontaneously result in the integration of said second progeny vector into the bacterial genome by homologous recombination and loss of the first progeny vector from the cells with a certain frequency.

In order to facilitate selection for cells in which the second progeny vector has been integrated in the genome, this vector is preferably provided with a selectable marker. In this case, the cells may be cultured under selective conditions which is to say that only cells in which the selectable marker is maintained will survive. The selectable marker may be a gene coding for a product which confers antibiotic resistance to the cell or which confers prototrophy to an auxotrophic strain (e.g. dal genes introduced in a dal strain; cf. B. Diderichsen in *Bacillus: Molecular Genetics and Biotechnology Applications*, A. T. Ganesan and J. A. Hoch, Eds., Academic Press, 1986, pp. 35–46). Cells surviving under these conditions will either be cells containing the parental plasmid vector or containing both progeny vectors formed upon replication of the parental vector in the cell, or cells in which the second progeny vector comprising the DNA construct of the invention has been integrated. It has surprisingly been found that the parental vector and the first progeny vector are eventually lost whereas the second progeny vector comprising the DNA construct of the invention is spontaneously integrated in the host genome at a high frequency.

If it is desired to improve the efficiency with which integration of the DNA construct takes place, one may utilise, as the parental vector, a plasmid which is able to replicate under certain (permissive) conditions and unable to replicate under other (non-permissive) conditions. The plasmid may, for instance, be one which is temperature-sensitive for replication. Thus, in an embodiment of the method of the invention, the parental vector is one which is unable to replicate at increased temperatures, which yet permit growth of the host cell. The bacterial cells are initially cultured at a temperature permitting plasmid replication and formation of the two progeny vectors and subsequently, after integration of the second progeny vector, comprising the DNA construct of the invention, into the bacterial genome may have taken place, cultured at a temperature which does not permit plasmid replication so that the first progeny vector as well as the parental vector are lost from the cells. The cultivation at the non-permissive temperature is conducted under selective conditions to ensure that only cells containing the integrated DNA construct, including an appropriate selectable marker, will survive.

Another way of increasing the efficiency of integration and subsequent loss of the first progeny vector from the cells may be to treat the cells transformed with the parental vector with a plasmid-curing agent, e.g. novobiocin (Gadd, I. et al., 1987. Zbl. Bakt. Hyg. A. 265, 136–145), after culturing the host cells under selective conditions as described above.

It may be possible to employ replication origins from two different plasmids on the same parental vector, provided that these are sufficiently similar to each other to be functional with the same replication factor(s) which should be able to initiate replication from both the first and the second origin of replication. Alternatively, the plasmid vector should contain homologous regions in order to be able to undergo homologous recombination as described above. It is, however, preferred that the first origin of replication (and the gene coding for the replication factor associated therewith) is derived from the same plasmid as the second origin of replication in order to ensure that the replication mechanism on which the present invention is based will function optimally.

Out of practical considerations, it may be preferred to make the initial construction of the plasmid vector in an organism in which replication from the first and second origins of replication cannot be initiated or in which the rate of replication from these origins is very low. The plasmid vector may therefore be a shuttle vector provided with an additional origin of replication which makes the vector able to replicate in two different organisms. The additional origin of replication may, for instance, be one which is functional in *Escherichia coli*, this organism being well described and conventionally used for recombinant DNA experimentation and therefore suitable for constructing plasmids by recombinant DNA techniques. The shuttle vector may also comprise an additional selectable marker, e.g. an antibiotic resistance gene, for selection of the vector in *E. coli*. The additional origin of replication and selectable marker should preferably follow the first origin and/or the replication factor(s), but precede the second origin so that, on replication of the vector from the first and second origins, these additional sequences will be carried by the first progeny vector which is eventually lost from the bacterial cell transformed with the parental vector.

In an alternative method of producing the bacterial cell of the invention, host cells are transformed with a first DNA vector comprising a first origin of replication associated with a functional gene encoding a factor required for plasmid replication from said first origin of replication, and subsequently or simultaneously, by cotransformation, with a second DNA vector comprising a second origin of replication lacking an associated functional gene encoding a factor required for plasmid replication from the second origin of replication, as well as a DNA sequence of interest, and a DNA sequence which is homologous with a region of the genome of the cell. The second DNA vector is also preferably provided with a selectable marker. The resulting cells containing the first and second DNA vectors are then cultured, preferably under selective conditions as described above, which eventually leads to integration of said second DNA vector into the bacterial genome by homologous recombination and loss of the first DNA vector for which there is no selection. As in the method described above initially employing a single plasmid vector, the first DNA vector may be one the replication of which is dependent on permissive and non-permissive conditions for culturing cells transformed with the vector. Thus in the method of the invention, the first DNA vector may be one which is unable to replicate at increased temperatures, which yet permit growth of the host cells, and the bacterial cells are initially cultured at a temperature permitting plasmid replication and subsequently, after integration of the second DNA vector into the bacterial genome, cultured at a temperature which does not permit plasmid replication so that the first DNA vector is lost from the cells and under selective conditions so that only cells in which the second DNA vector is integrated, are able to survive. Similarly, the transformed cells may be treated with a plasmid-curing agent as described above.

An intermediate formed in both of the methods of constructing a cell containing the integrated non-replicative DNA construct discussed above is a bacterial cell which comprises a first DNA vector comprising a first origin of replication associated with one or more functional gene(s) encoding the factor(s) required for plasmid replication from said first origin of replication, and a second DNA vector comprising a second origin of replication, as well as a DNA sequence of interest, and a DNA sequence which is homologous with a region of the genome of the cell, said second vector lacking a functional gene coding for a replication factor required for replicatin from the origin of replication carried on said second vector.

In order to obtain an origin of replication on the second DNA vector which lacks a functional gene coding for a replication factor required for replication from said origin, it is possible to delete this gene from the vector or to modify it in the ways indicated above. In particular when using two different origins of replication, the first DNA vector may also be provided with a gene coding for a replication factor required to initiate replication from the second origin of replication. In this way, replication of the second DNA vector depends on the second replication factor produced from the first DNA vector, and the second vector becomes non-replicative when the first vector is lost from the cell. However, the first and second origin of replication may also be derived from the same plasmid, in which case only one gene coding for an intact replication factor is required on the first vector.

Although, for the purpose of the present invention, the bacterial cell into which the plasmid vector or the first and second DNA vector are transformed may be both gram-negative and gram-positive, it is preferably a cell of a gram-positive bacterium as it is generally easier to obtain extracellular expression of polypeptides from gram-positive organisms than from gram-negative ones. Thus, the bacterium may be of a strain belonging to the genus Bacillus or Streptomyces, in particular a strain of *Bacillus licheniformis, Bacillus lentus, Bacillus brevis, Bacillus stearothermophilus, Bacillus alkalophilus, Bacillus amyloliquefaciens, Bacillus coagulans, Bacillus subtilis* or *Streptomyces lividans*.

The present invention is currently believed to be the only efficient method of providing stable homologous integration of DNA sequences of interest in genomes of bacteria which cannot be transformed by being made competent (or, at least, in which natural competence mechanisms have yet to be demonstrated), but which may be transformed by techniques including, for instance, protoplast formation or electroporation, e.g. certain strains of *Bacillus licheniformis* or *Bacillus lentus*. The present method is therefore of particular interest with respect to such organisms in which the transformation frequency is low, typically 10–50 transformants per µg of DNA (contrary to, e.g., transformation of competent *E. coli* or *B. subtilis* cells, where the number of transformants is typically on the order of $10^6$–$10^8$ per µg of DNA), which makes the sucessful transformation and stable integration of DNA in these organisms particularly important.

In the bacterial cell of the invention, the DNA sequence of interest is advantageously one which codes for a polypeptide of interest, and the present invention consequently further relates to a process for producing a polypeptide of interest, comprising culturing a bacterial cell according to the invention containing an integrated DNA sequence which codes for said polypeptide under conditions conducive to the production of the polypeptide and recovering the resulting polypeptide from the culture. The polypeptide produced by the present process may be any polypeptide advantageously produced in bacteria such as an enzyme, e.g. a protease, amylase or lipase.

DESCRIPTION OF PREFERRED EMBODIMENTS OF THE INVENTION

A large family of plasmids from gram-positive bacteria replicate by the so-called "rolling circle replication" mechanism generating single-stranded DNA as a replication intermediate. Replication is initiated when a plasmid-encoded protein, Rep, recognizes an origin of replication sequence (the plus origin) and produces a nick in one of the DNA strands (the plus strand). The plus strand is then displaced, and a new plus strand is polymerized from the nick by 3'-OH extension. When the Rep protein subsequently recognizes a termination sequence (which overlaps the plus origin), it produces a second nick at the same position as the first one to generate a fully replicated strand and a single-stranded DNA monomer of the displaced strand the ends of which are ligated to form a circular molecule. Host factors then ensure the conversion of the single-stranded DNA molecule to double-stranded DNA (for a more detailed description of this type of plasmid, see A. Gruss and S. D. Ehrlich, *Microbiological Reviews* 53(2), June 1989, pp. 231–241). For the present purpose, plasmids with this replication system are termed single-stranded DNA plasmids.

It has surprisingly been found that the rolling circle replication mechanism may be utilised according to the invention to produce a bacterial cell according to the invention which harbours a DNA construct comprising, apart from a DNA sequence of interest and a DNA sequence which is homologous to a region of the genome of the cell, a plus origin of replication from a single-stranded DNA plasmid, lacking a functional rep gene cognate to the plus origin of replication.

This bacterial cell may be constructed by the method of the invention using a parental plasmid vector which comprises (i) a first plus origin from a single-stranded DNA plasmid; (ii) a functional red gene cognate to the first plus origin; (iii) a second plus origin from a single-stranded DNA plasmid in the same orientation as the first plus origin (iv) a DNA sequence of interest, and (v) a DNA sequence which is homologous with a region of the genome of a cell intended for introduction of the plasmid vector, said parental vector lacking, in the region between the second and the first plus origin in the same orientation as above, a functional red gene cognate to the second plus origin.

On replication of the parental vector, the first and second progeny DNA vectors are formed, presumably by the following mechanism:

The Rep protein initiates replication by producing a nick at the first plus origin, and proceeds to make a nick at the second plus origin. The displaced strand is religated to form a first progeny vector comprising a first plus origin of replication from a single-stranded DNA plasmid and a functional red gene cognate to the first plus origin. Similarly, the Rep protein proceeds from the second plus origin to make a nick at the first plus origin thus forming, on religation of the displaced strand and conversion of the single-stranded DNA to double-stranded DNA, a second progeny vector comprising a second plus origin of replication from a single-stranded DNA plasmid lacking a functional rep gene cognate to the second plus origin of replication, as well as a DNA sequence of interest, and a DNA sequence which is homologous with a region of the genome of said cell. As the second progeny vector does not comprise a functional rep gene, replication of this molecule depends entirely on the Rep protein supplied in trans from either the first progeny vector or from the parental vector.

Alternatively, the two progeny vectors could also be formed as a result of recombination between the homologous DNA regions including and/or adjacent to the two origins present on the parental vector.

A second progeny vector without a functional replication origin may be formed if the first plus origin in the parental plasmid described above is replaced by a small DNA fragment derived from the origin region which is sufficient to ensure termination of plasmid replication but too small to constitute a functional origin. Such fragments have been identified in pUB110 (Boe et al., 1989, J. Bacteriol., 171, 3366–3372) and in pC194 (Gros et al., 1987, EMBO J., 6, 3863–3869).

The bacterial cell may alternatively be constructed by a method of the invention comprising transforming the host cell with a first DNA vector comprising a first plus origin of replication from a single-stranded DNA plasmid associated with a functional rep gene, and subsequently or simultaneously, by cotransformation, transforming the host cell with a second DNA vector comprising a second plus origin of replication from a single-stranded DNA plasmid lacking a functional rep gene cognate to the second plus origin of replication, but comprising a DNA sequence of interest, and a DNA sequence which is homologous with a region of the genome of said cell. The second DNA vector is maintained in the cell due to the presence of Rep protein supplied from the first DNA vector.

When the parental vector or second DNA vector comprises a modified rep gene, the second plus origin may precede or be located in the modified rep gene. As described above, the second plus origin may be derived from the same or a different plasmid as the first plus origin. In cases where the first and second plus origins are derived from different plasmids so that replication will not be initiated from both origins by means of the same Rep protein, the first DNA vector may additionally contain a rep gene encoding an active Rep protein capable of initiating replication from the second plus origin. The parental vector or second DNA vector may also comprise a selectable marker as described above.

In a favoured embodiment for promoting the integration process, a vector may be employed the replication of which is dependent on permissive conditions, including the temperature at which host cells are cultured. Thus, when a host bacterium containing the first and second DNA vectors is cultured at the permissive temperature for plasmid replication, the Rep protein produced from the first DNA vector will serve to maintain the second DNA vector in the cell. However, at non-permissive temperatures at which the first DNA vector is unable to replicate, the first vector and consequently the Rep protein produced from it will be lost from the cell so that the second DNA vector is no longer able to replicate either. By continued cultivation under selection pressure, e.g. in the presence of an antibiotic, only those cells survive which in their genome contain the inserted DNA construct of the invention, including a gene coding for a selectable marker.

It should be noted that once the DNA construct has been integrated in the genome of the host cell, this may be cultured in the absence of selection pressure without consequent loss of the DNA construct or parts thereof from the cell. This is believed to be ascribable to the fact that the integrated DNA is incapable of autonomous replication, but is replicated together with the host genome. The lack of autonomous replication of the integrated DNA implies that there is no formation of the single-stranded DNA intermediate which is believed to be responsible for the recombination process whereby integrated DNA is excised from the host genome (cf. Ph. Noiret et al., *J. Mol. Biol.* 196, 1987, pp. 39–48; and M. Young and S. D. Ehrlich, *J. Bacteriol.* 171(5), May 1989, pp. 2653–2656).

It has been found possible to amplify the integrated DNA construct by culturing transformed cells under increased selection pressure, e.g. at increased concentrations of an antibiotic. It has previously been found (cf.) that in the absence of selection pressure such amplified copies are frequently lost from the cells. Contrary to this, the present invention provides a bacterial cell in which amplified copies of integrated DNA sequences may be stably maintained in host cells because, as explained above, the integrated DNA is non-replicative. Although the present invention has mainly been described above as suitable for the integration of heterologous DNA sequences, it should be noted that the present method is also suitable for obtaining an amplified copy number of a gene which is homologous to the host cell in order to increase its production of a specific gene product.

BRIEF DESCRIPTION OF THE DRAWINGS

The invention is further illustrated with reference to the accompanying drawings wherein
FIG. 28 shows a restriction map of plasmid pSJ1259a;
FIG. 30 shows a restriction map of plasmid pSJ1555a.

In all figures, arrows denote the direction of transcription.

To improve readability the replicational origins (+ori pUB110, +ori pE194, ori pUC19) are indicated by the actual start site for replication, even though a functional origin consists of a larger DNA region.

The invention is further described in the following examples which are not intended to be in any way limiting to the scope and spirit of the invention as claimed.

MATERIALS AND METHODS

Figure 6:
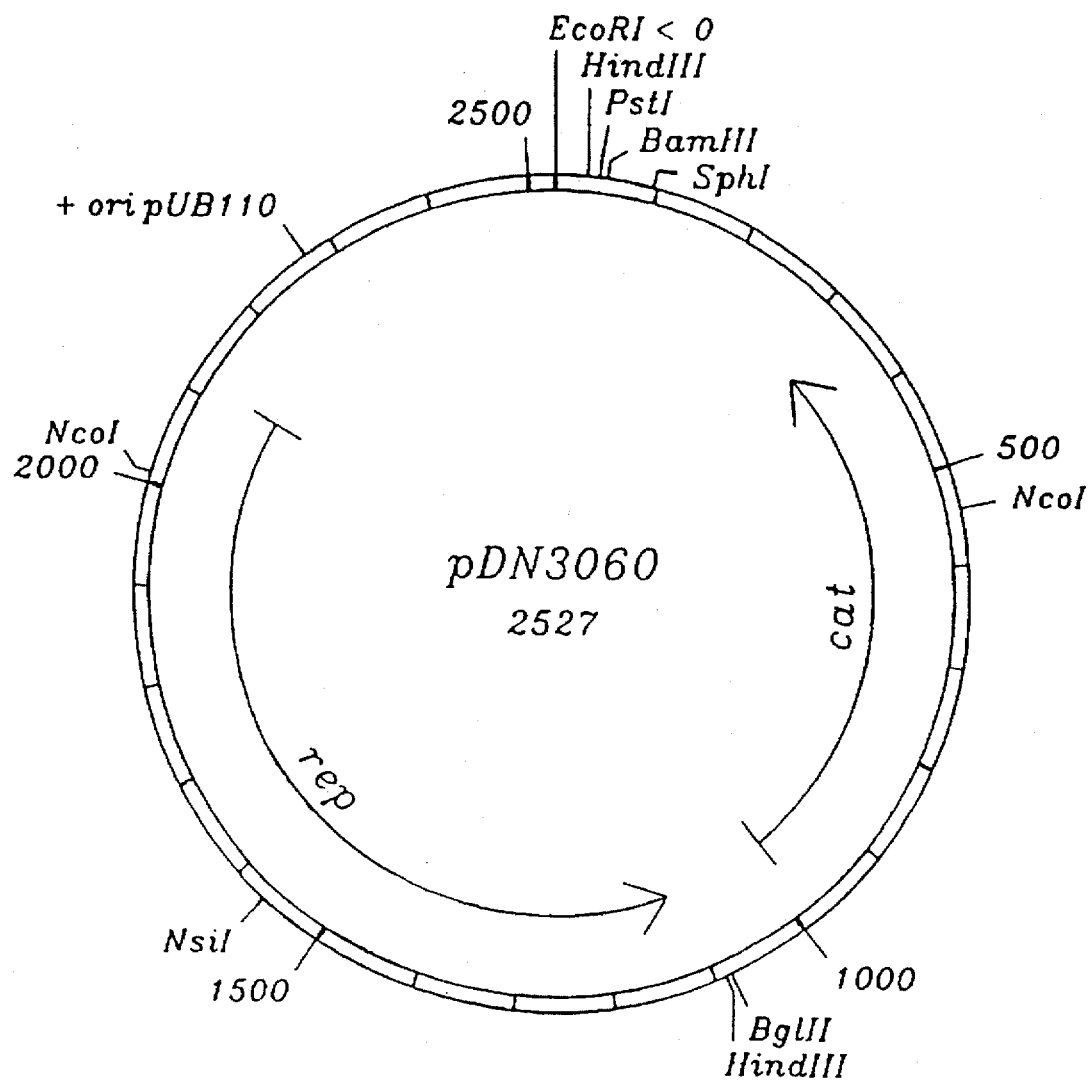
FIG. 6 shows a restriction map of plasmid pDN3060.
Figure 13:
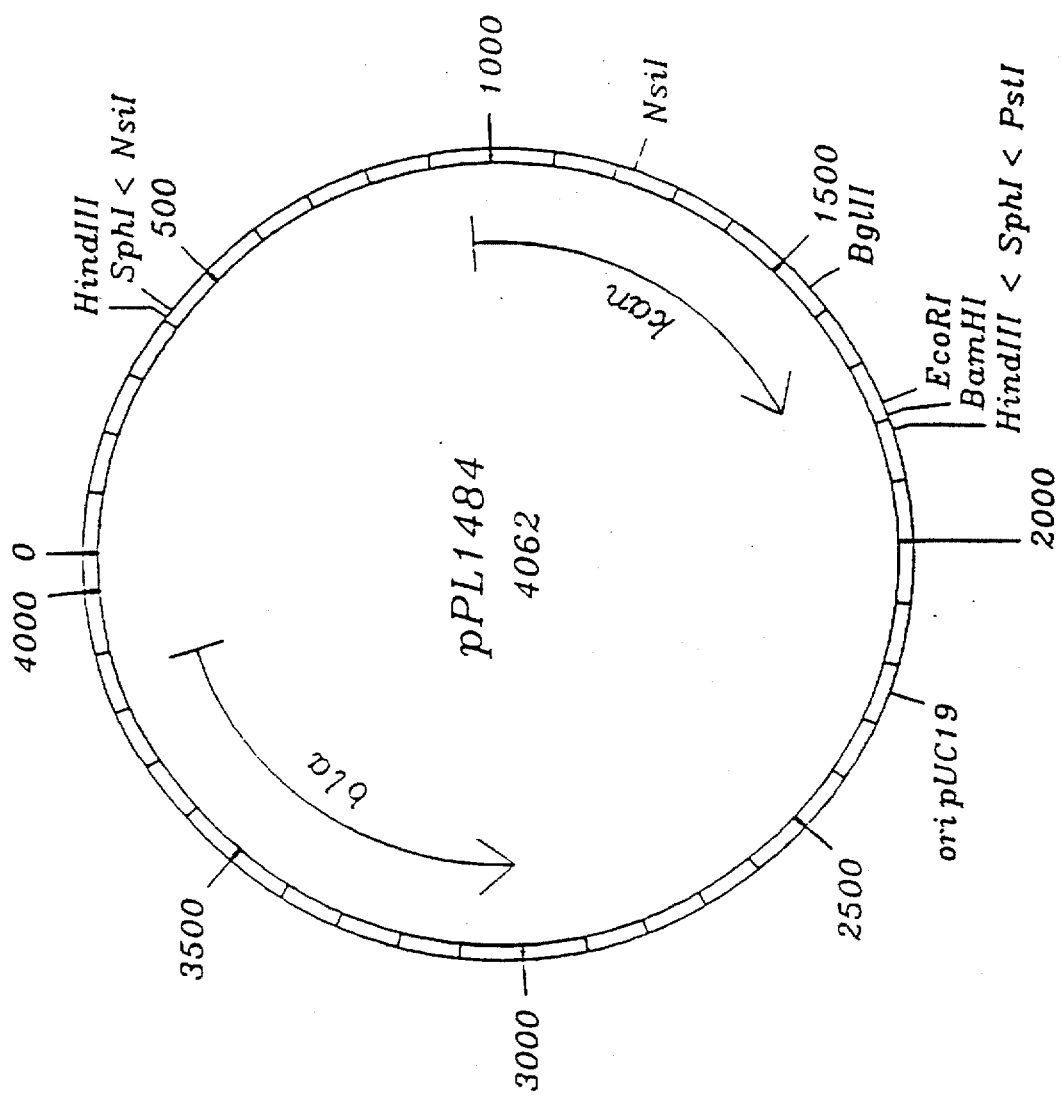
FIG. 13 shows a restriction map of plasmid pPL1484.
Figure 17:
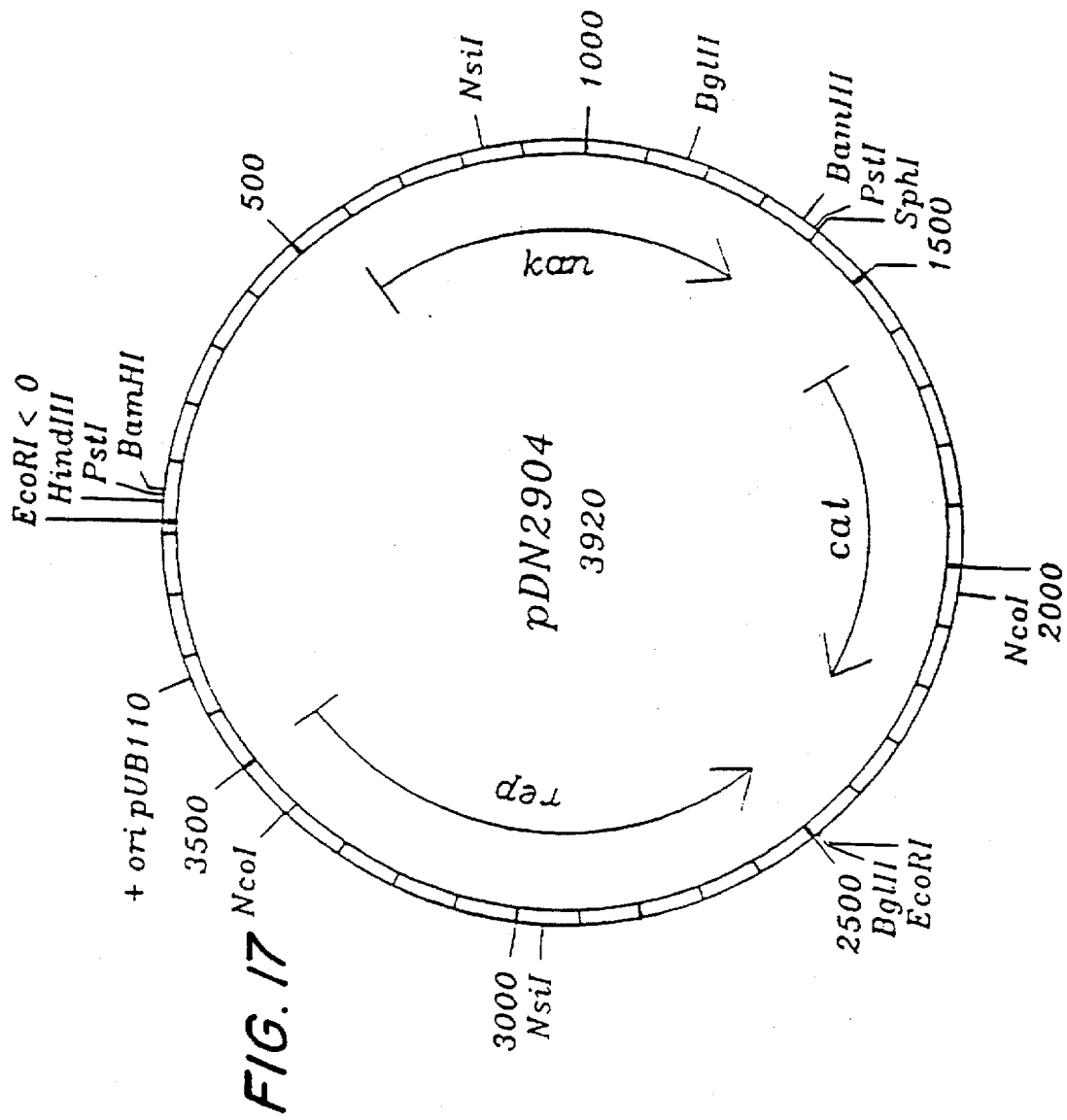
FIG. 17 shows a restriction map of plasmid pDN2904.
Figure 22:
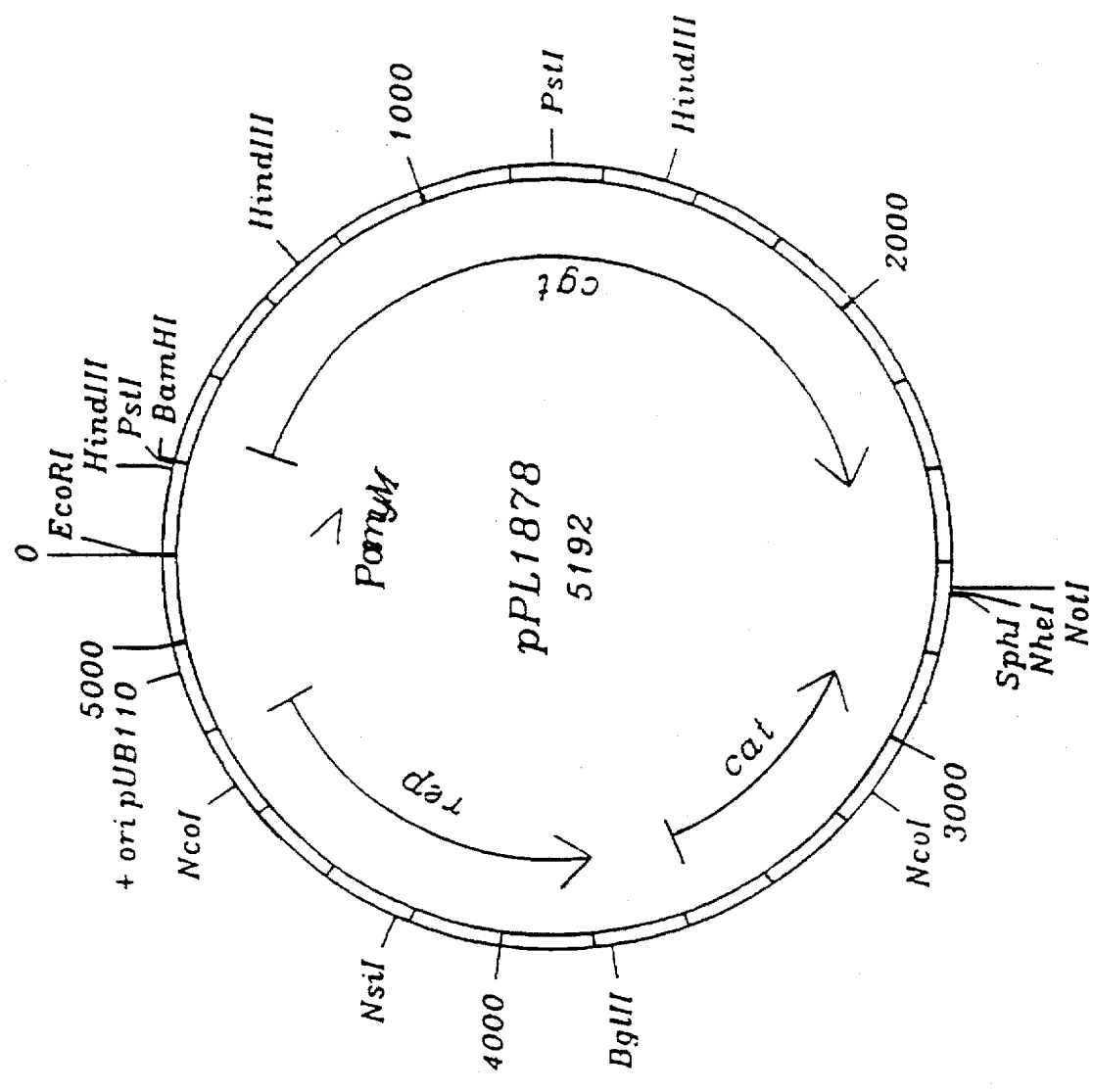
FIG. 22 shows a restriction map of plasmid pPL1878.

Plasmids pBD64: described in Gryczan et al., 1980.

pDN3060: A cloning vector derived from the Bacillus plasmid pDN1050 (Diderichsen, B., 1986) by insertion of synthetic oligonucleotides containing a number of useful restriction sites. The restriction map is shown in FIG. 6.

pDN2904: A derivative of the Bacillus plasmid pUB110 (Gryczan et al., 1978), containing both a chloramphenicol resistance gene and a kanamycin resistance gene. The restriction map is shown in FIG. 17.

pPL1484: A pUC19 (Yanisch-Perron et al., 1985) derivative containing a modified polylinker region into which was inserted a 1.4 kb BamHI fragment from pDN2904 containing the kanamycin resistance gene. The restriction map is shown in FIG. 13.

pPL1878: pDN1380 (described in Diderichsen and Christiansen, 1988) containing a 2.4 kb HaeII-SphI fragment encoding a Cyclodextrin Glycosyl Transferase (CGTase) originating from Thermoanaerobacter sp. ATCC 53627. The gene was initially cloned into the *E. coli* plasmid pBR322 on a 12.8 kb EcoRI fragment (Starnes et al., 1989). The restriction map is shown in FIG. 22.

Strains

*E.coli* SJ 6: a restriction-deficient derivative of MC1000 (Diderichsen et al., 1990) *Bacillus subtilis* DN1885: an amyE, amyR2, spo$^+$, Pro$^+$ derivative of *B. subtilis* 168. (Diderichsen et al., 1990).

*Bacillus subtilis* DN1686: A spo derivative of DN1280 containing a chromosomal deletion in the dal gene (Diderichsen, 1986).

*Bacillus licheniformis* ATCC 9789
*Bacillus lentus* NCIB 10309

Media

| TY: | Trypticase | 20 g/l |
| --- | --- | --- |
| | Yeast extract | 5 g/l |
| | FeCl$_2$.4H$_2$O | 6 mg/l |
| | MnCl$_2$.4H$_2$O | 1 mg/l |
| | MgSO$_4$.7H$_2$O | 15 mg/l |
| | pH | 7.3 |
| TY9: | As TY media but the pH was adjusted to 8,5 by adding NaHCO$_3$ (0,1M) | |
| TY9 agar: | Trypticase | 20 g/l |
| | Yeast extract | 5 g/l |
| | FeCl$_2$.4H$_2$O | 6 mg/l |

|      |                                      |          |
|------|--------------------------------------|----------|
|      | MnSO$_4$.4H$_2$O                     | 1 mg/l   |
|      | MgSO$_4$.7H$_2$O                     | 15 mg/l  |
|      | Bacto agar                           | 5 g/l    |
|      | Adjusted to pH 8,5 with NaHCO$_3$ (0,1M) |       |
| BPX: | Potato starch                        | 100 g/l  |
|      | Barley flour                         | 50 g/l   |
|      | BAN 5000 SKB                         | 0.1 g/l  |
|      | Sodium caseinate                     | 10 g/l   |
|      | Soy Bean Meal                        | 20 g/l   |
|      | Na$_2$HPO$_4$, 12 H$_2$O             | 9 g/l    |
|      | Pluronic                             | 0.1 g/l  |
| LB agar: | Bacto-tryptone                   | 10 g/l   |
|      | Bacto yeast extract                  | 5 g/l    |
|      | NaCl                                 | 10 g/l   |
|      | Bacto agar                           | 15 g/l   |
|      | Adjusted to pH 7.5 with NaOH         |          |

GENERAL METHODS

The experimental techniques used to construct the plasmids were standard techniques within the field of recombinant DNA technology, cf. T. Maniatis et al., *Molecular Cloning: A Laboratory Manual*, Cold Spring Harbor, N.Y., 1982.

Restriction endonucleases were purchased from New England Biolabs and Boehringer Mannheim and used as recommended by the manufacturers. T4 DNA ligase was purchased from New England Biolabs and used as recommended by the manufacturer.

Preparation of plasmid DNA from all strains was conducted by the method described by Kieser, 1984.

Transformation of *E. coli*

Cells of *E. coli*. were made competent and transformed as described by Mandel and Higa, 1970, or were transformed by electroporation as described in the manual for the BIO-RAD Gene Pulser electroporation apparatus.

Transformation of *B. subtilis*

Competent cells were prepared and transformed as described by Yasbin et al., 1975.

Transformation of *B. licheniformis*

Plasmids were introduced into *B. licheniformis* by polyethylene glycol-mediated protoplast transformation as described by Akamatzu, 1984.

Transformation of *B.lentus*

Plasmids were introduced into *B.lentus* by protoplast transformation according to a slightly modified procedure by Akamatzu (1984). The modifications were a higher pH in the regeneration medium e.g. the HCP 1,5 medium were buffered to pH 8,5 by adding 0,1M NaHCO$_3$ to the medium.

EXAMPLE 1

Stable integration of a non-replicative DNA molecule in the *Bacillus lentus* chromosome.

Cloning of the Subtilisin 309 gone

Figure 4:
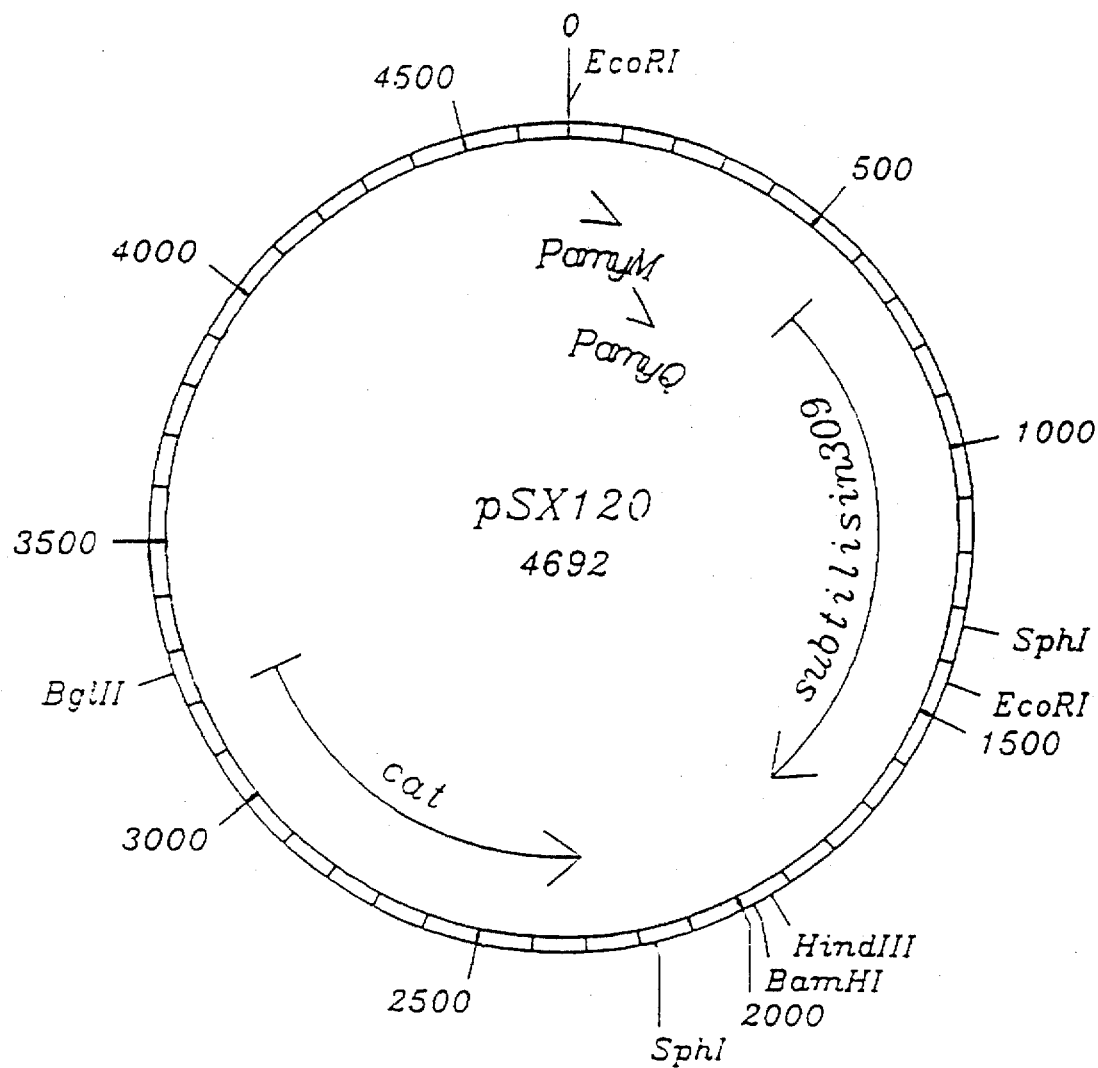
FIG. 4 shows a restriction map of plasmid pSX120.

The gene coding for the protease designated subtilisin 309 was cloned from an isolate of the *B.lentus* strain NCIB 10309 as described in WO 89/06279. Further subcloning resulted in the plasmid pSX120, which contains the replication origin of pUB110, the chloramphenicol resistance gene (cat) from pC194, two promoters P$_{AmyM}$ and P$_{AmyQ}$ and the gene encoding for the subtilisin 309 protease. (See FIG. 4 and International Patent Application No. PCT/DK90/00164)

Construction of the integration plasmid pPL2002.

Plasmid pDN3000 was constructed by restricting pUC19 (Yanisch-Perron et. al. ) with EcoRI and inserting the following oligonucleotide sequence (prepared by the phosphoamidite method described by Beaucage and Caruthers, *Tetrehedron letters* 22, 1981, pp. 1859–1869, on an automatic DNA synthesizer) (SEQ ID NO:1)

Figure 1:
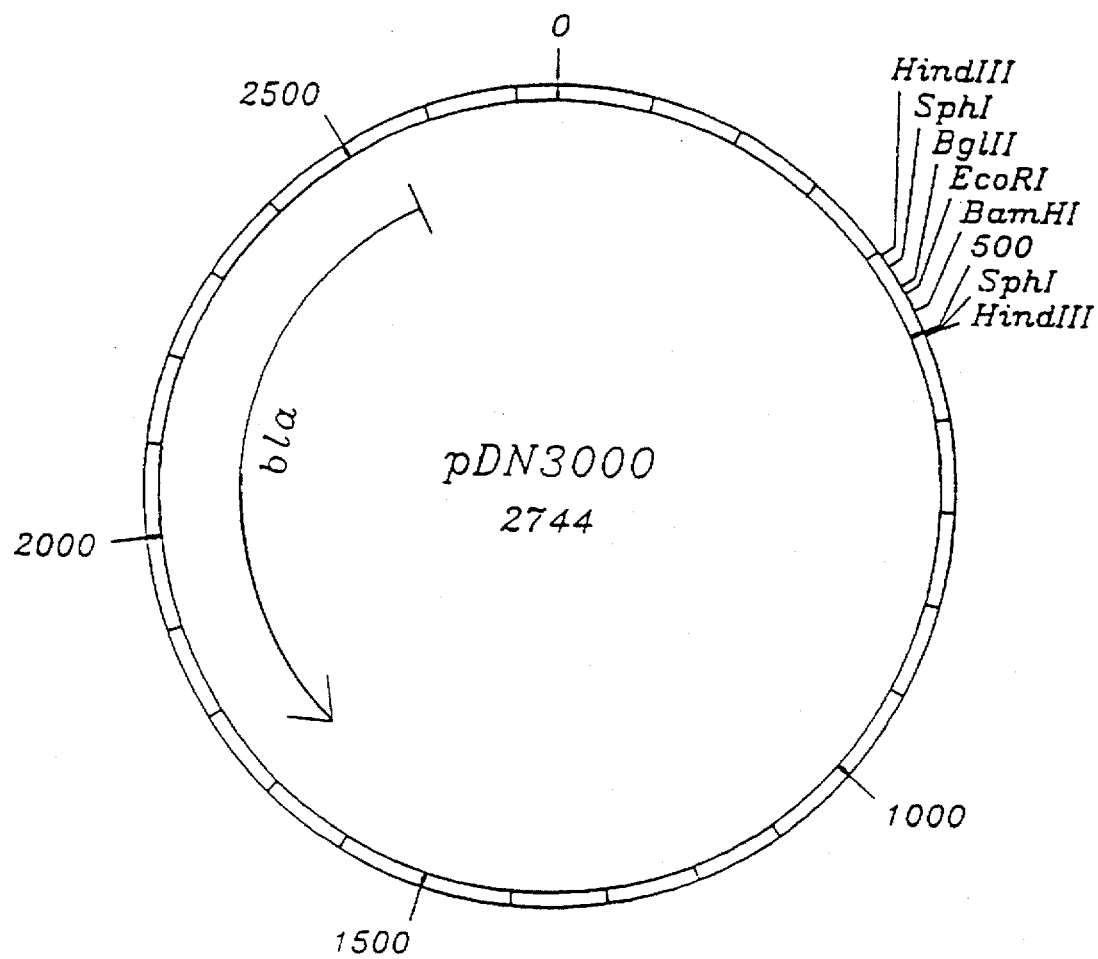
FIG. 1 shows a restriction map of plasmid pDN3000.

AATTGATCAAGCTTTAAATGCATGCTAG-
CAACGCGGCCGCCAACCTCGAGATCTCATG
CTAGTTCGAAATTTACGTACGATCGT-
TGCGCCGGCGGTTGGAGCTCTAGAGTACTTAA into the linearized pUC19 followed by ligation. The ligation mixture was then used to transform competent *E.coli* SJ6 cells and transformants were selected on LB plates containing 100 ug/ml ampicillin. The orientation of the inserted linker in pDN3000 is as indicated by the orientation of the restriction sites in FIG. 1.

Figure 2:
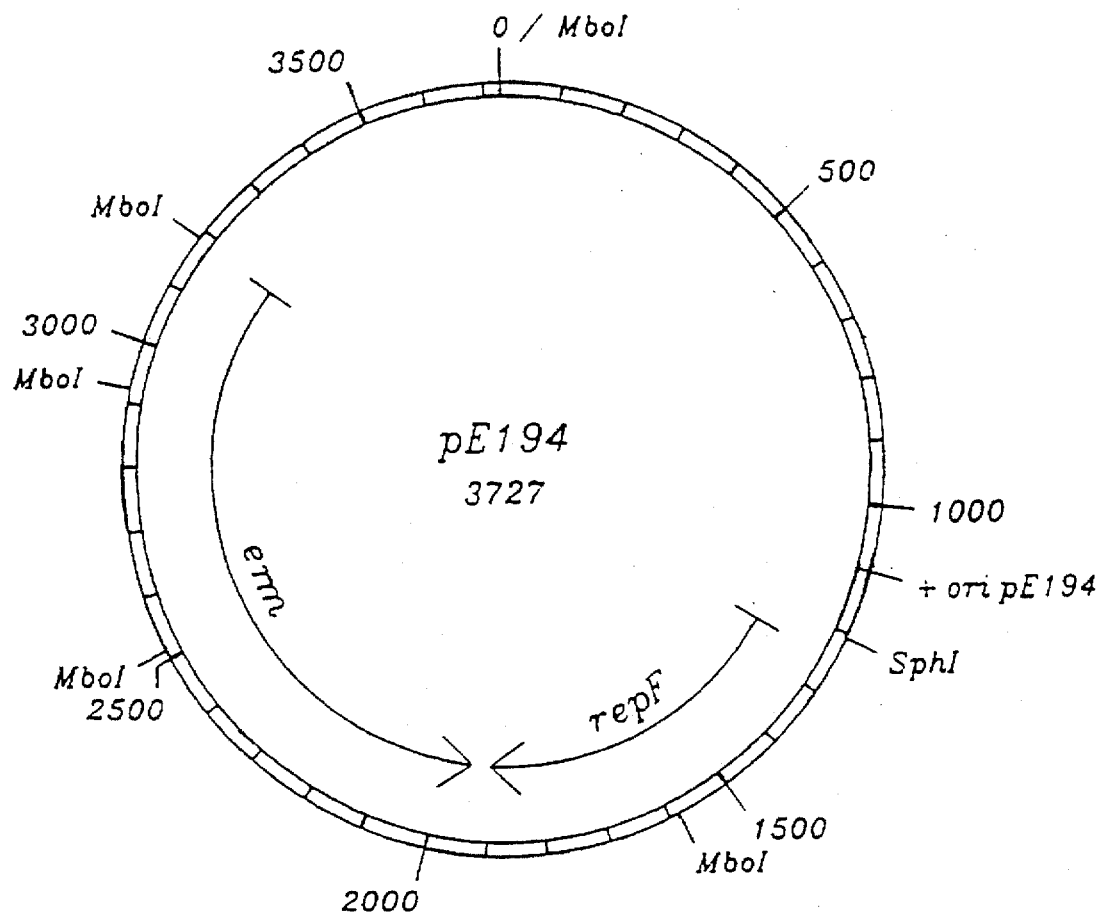
FIG. 2 shows a restriction map of plasmid pE194.
Figure 3:
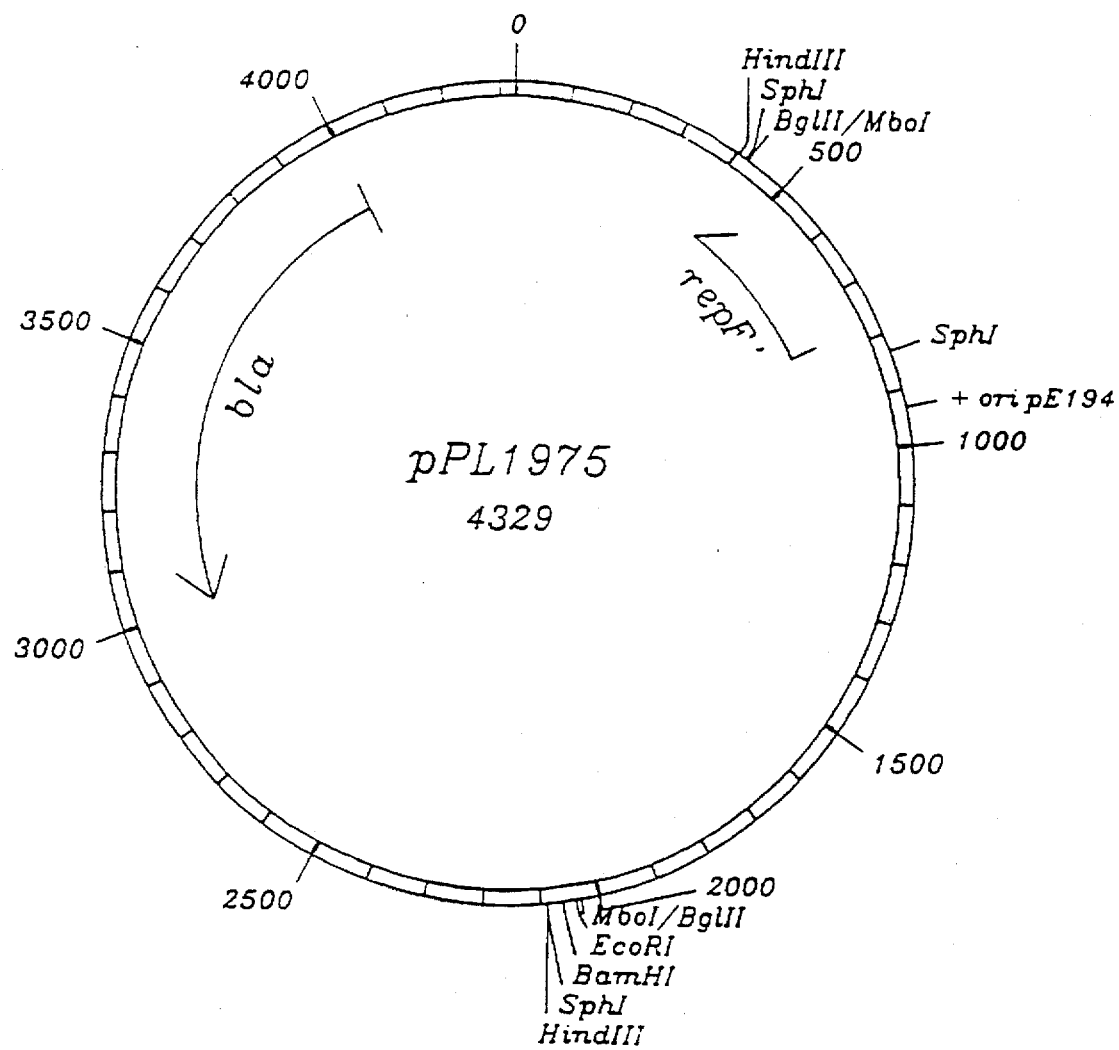
FIG. 3 shows a restriction map of plasmid pPL1975.

Plasmid pPL1975 was constructed by restricting pDN3000 with BglII followed by ligation of this linearized plasmid to the MboI fragment containing the DNA from position 1 to 1585 resulting from restriction of pE194 (FIG. 2, Horinouchi and Weisblum) with MboI. The ligation mixture was then used to transform competent *E.coli* SJ6 cells and transformants were selected on LB plates containing 100 ug/ml ampicillin. The orientation of the connection of these two fragments is as indicated in FIG. 3. pPL1975 thus contains a functional *E. coli* replication origin and a pE194 DNA fragment comprising an intact plus origin (+ori pE194) and a truncated repF gene (repF') ( Villafane et al., 1987).

Figure 5:
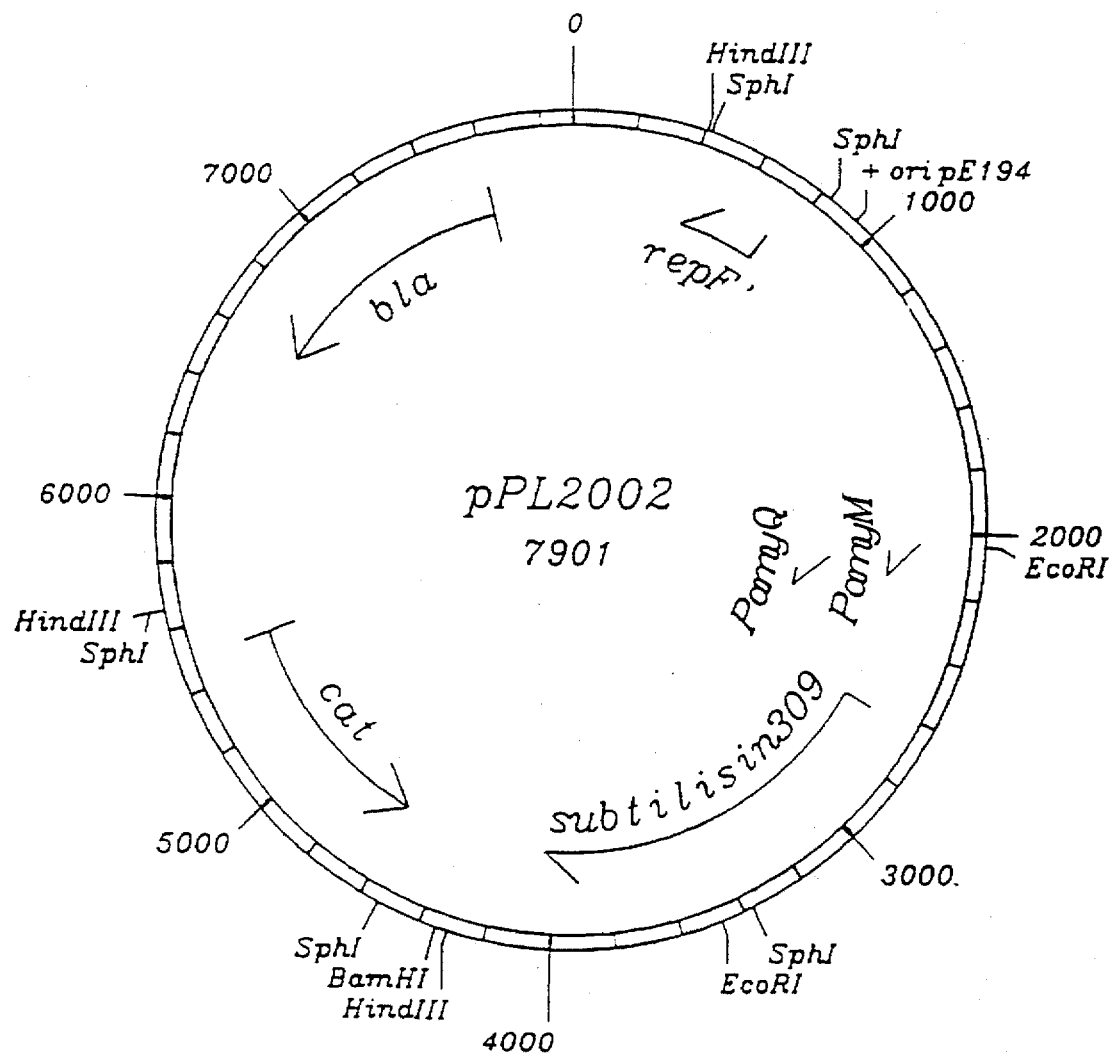
FIG. 5 shows a restriction map of plasmid pPL2002.

Plasmid pPL2002 (FIG. 5) was constructed by restricting pPL1975 (FIG. 3) by EcoRI and BamHI and ligating the linearized plasmid to the 3.3 kb EcoRI (partial), BglII fragment from pSX120 (FIG. 4) containing the subtilisin 309 gene and the cat resistance gene. The ligation mixture was then used to transform competent *E. coli* SJ6 cells and transformants were selected on LB plates containing 100 ug/ml ampicillin.

Stable integration of the pPL2002 plasmid into the chromosome of *B.lentus*.

An isolate of the *B.lentus* strain NCIB 10309 was transformed by protoplast transformation with the temperature sensitive plasmid pE194 (See FIG. 1) selecting for erythromycin resistance (5 ug/ml) at 30° C. (permissive temperature). The resulting strain was denoted PL2156.

PL2156 was then protoplast transformed with the plasmid pPL2002 selecting for chloramphenicol resistance (8 ug/ml) and erythromycin resistance (5 ug/ml) at 30° C. resulting in the strain PL2157 containing the two plasmids pE194 and pPL2002. In these cells the replication of the plasmid pPL2002 completely depends on the presence of the plasmid pE194 which encodes the for the pPL2002 replication, indispensable replication protein repF.

The strain PL2157 was grown overnight in TY9 medium and dilutions were plated on TY9 plates at 45° C. (nonpermissive temperature) selecting for chloramphenicol restance (10 ug/ml).

One of these chloramphenicol resistant colonies was denoted PL2158

Southern hybridization showed that, in the strain PL2158, the plasmid pPL2002 was integrated into the chromosome by homologous recombination between the plasmid-borne and chromosomal subtilisin 309 genes and thereafter amplified to approx. 4 copies. No evidence of complete pE194 plasmid sequences was detected.

The stability of the chromosomally integrated copies of pPL2002 in strain PL2158 was tested in large scale fermentations (1500 l) without any antibiotic.

After fermentation samples were diluted and plated on TY9 plates and 100 colonies were replicated to TY9 plates containing 10 ug/ml chloramphenicol. 98 of the tested colonies were still resistant to chloramphenicol indicating that the plasmid pPL2002 was still integrated in the chromosome. 20 of these colonies were then tested by Southern hybridisation which showed that the plasmid pPL2002 was still integrated, apparently in the same copy number (approx. 4 copies) in all of the tested colonies.

EXAMPLE 2

Construction of plasmid vectors containing two pUB110 origins of replication

Figure 7:
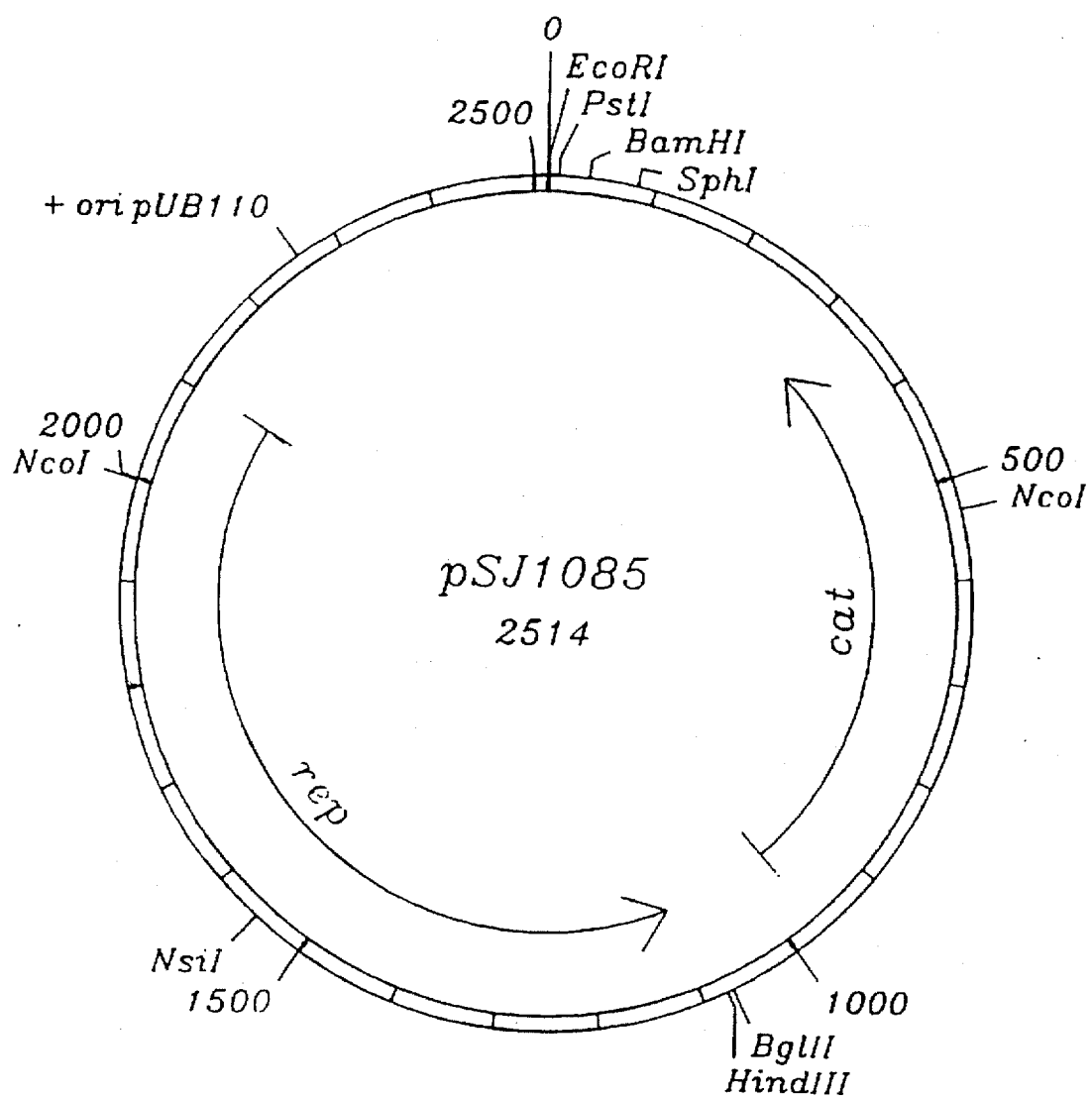
FIG. 7 shows a restriction map of plasmid pSJ1085.

Plasmid pSJ1085 (FIG. 7) was constructed by restricting pDN3060 (containing an origin of replication (+ ori pUB110) and rep gene (rep) from pUB110, and a chloramphenicol resistance gene (cat) from pC194) with BamHI and EcoRI and inserting the following oligonucleotide sequence (prepared by the phosphoamidite method described by Beaucage and Caruthers, Tetrahedron Letters 22, 1981, pp. 1859–1869, on an automatic DNA synthesizer) (SEQ ID NOS:2 and 3)

AATTCTGCAGATATCAAGATAAGAAA-GAACAAGTTCCG
GACGTCTATAGTTCTATTCTTTCTTGT-TCAAGGCCTAG into the linearized pDN3060 followed by ligation and transformation of B. subtilis DN1885.

Figure 8:
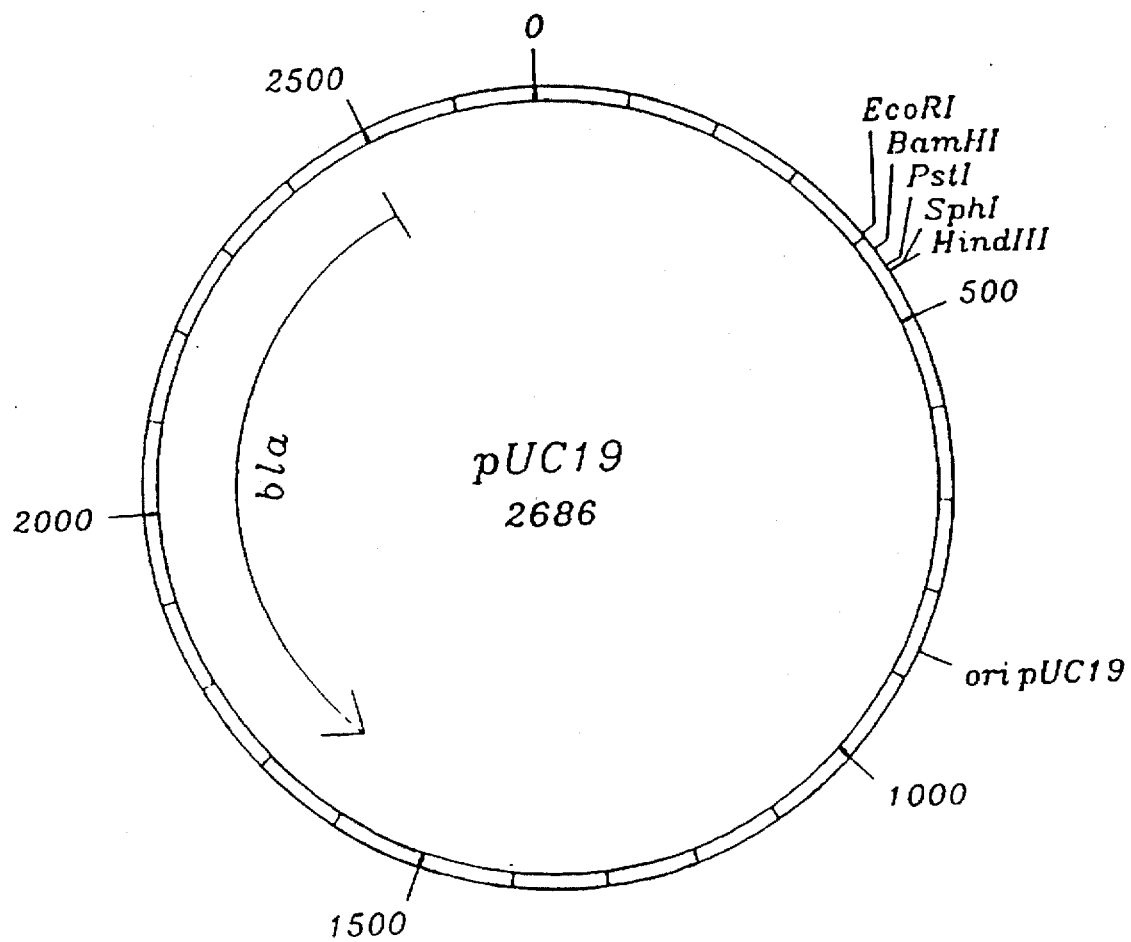
FIG. 8 shows a restriction map of plasmid pUC19.
Figure 9:
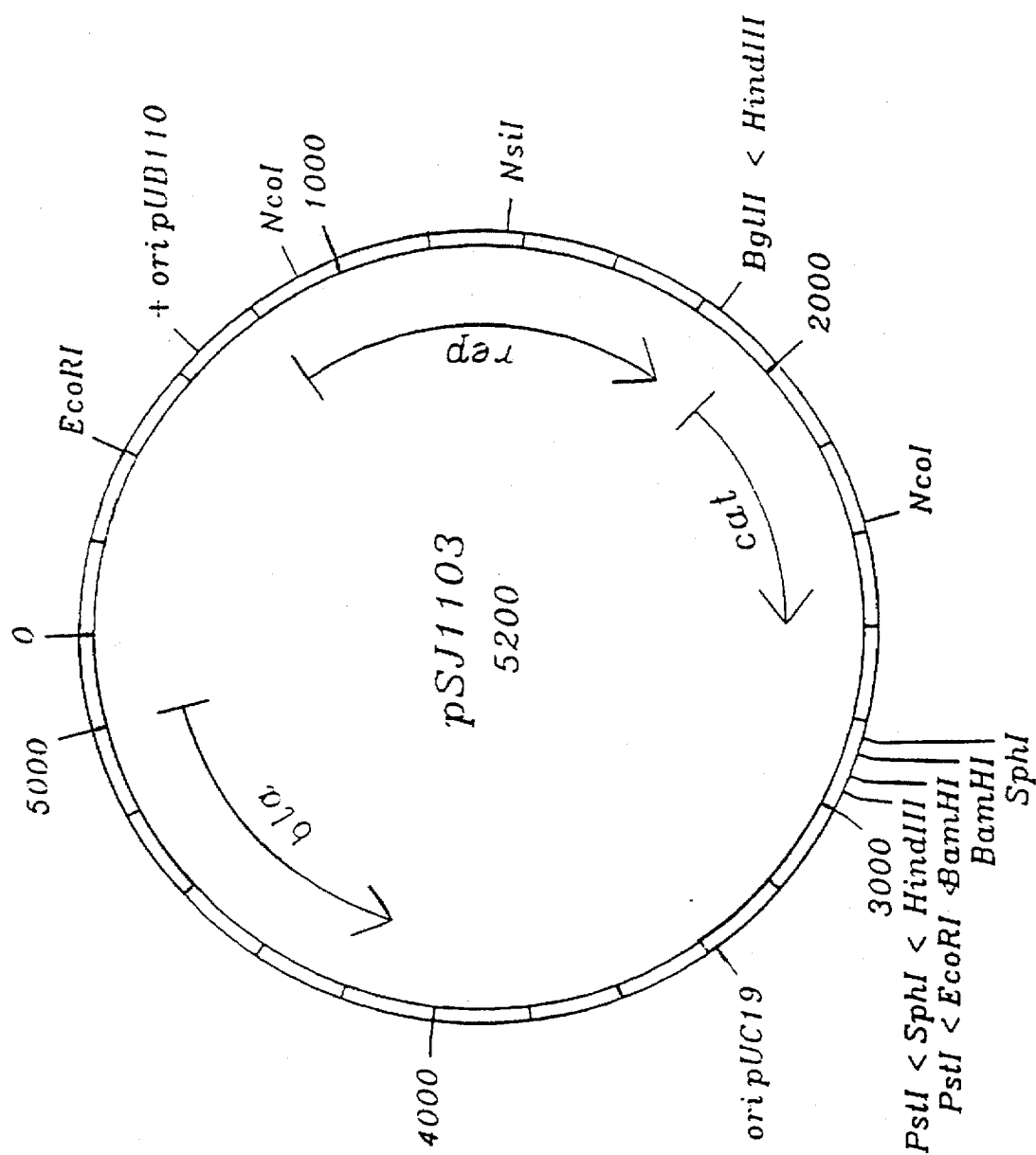
FIG. 9 shows a restriction map of plasmid pSJ1103.

Plasmid pSJ1103 (FIG. 9) was constructed by restricting pSJ1085 (FIG. 7) with EcoRI and inserting the entire linearized plasmid into the similarly restricted plasmid pUC19 (FIG. 8) followed by ligation and transformation of E. coli SJ6. The resulting plasmid pSJ1103 contains the plus origin and rep gene from pUB110, the cat gene from pC194, the pUC19 origin of replication (ori pUC19), and the β-lactamase (ampicillin resistance) gene (bla).

Figure 10:
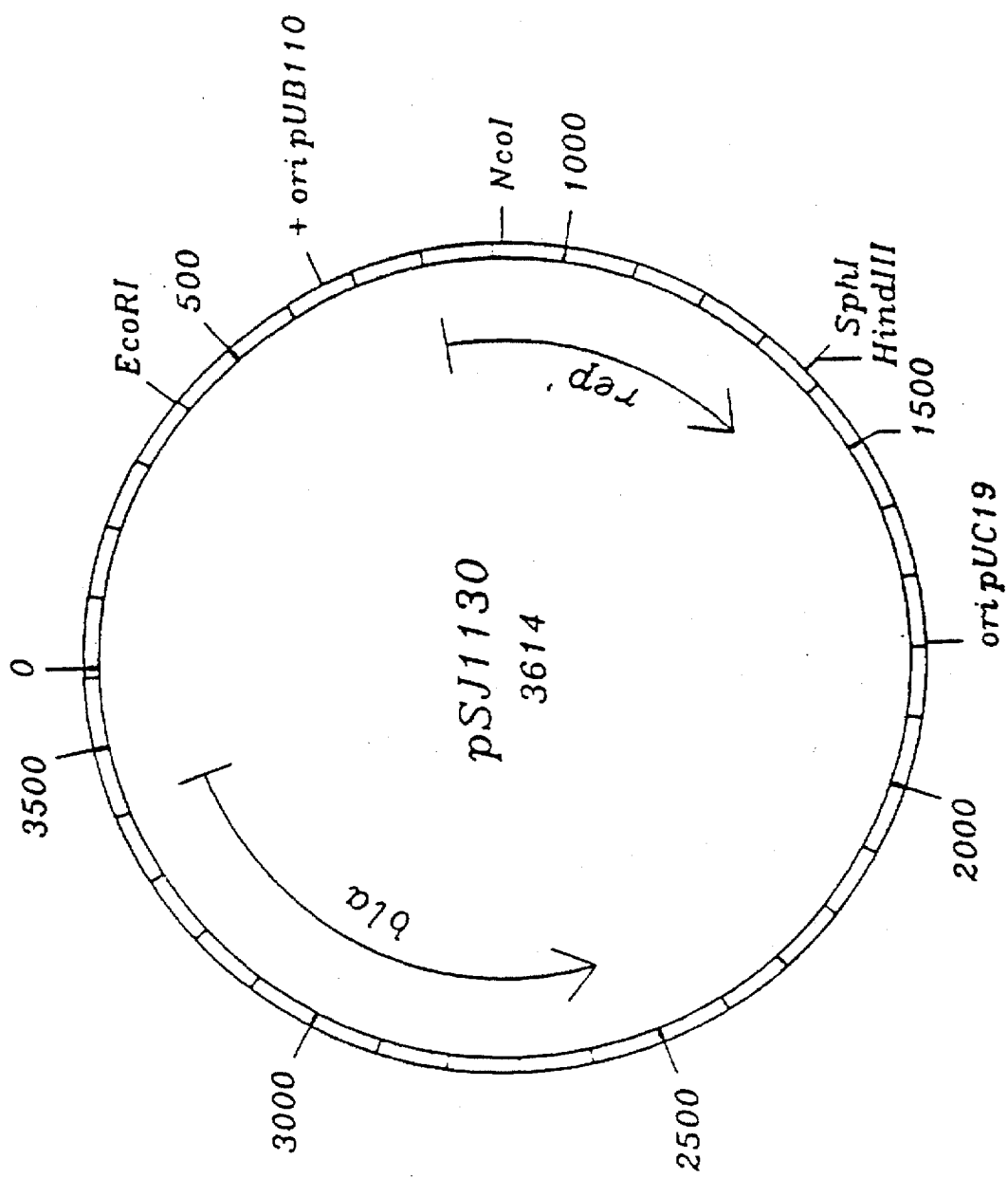
FIG. 10 shows a restriction map of plasmid pSJ1130.

Plasmid pSJ1130 (FIG. 10) was derived from pSJ1103 (FIG. 9) by deleting a 1.6 kb NsiI-PstI fragment, essentially resulting in a pUC19 plasmid containing a pUB110 plus-origin and a truncated rep gene (rep'). The plasmid was transformed into E. coli SJ6.

Figure 11:
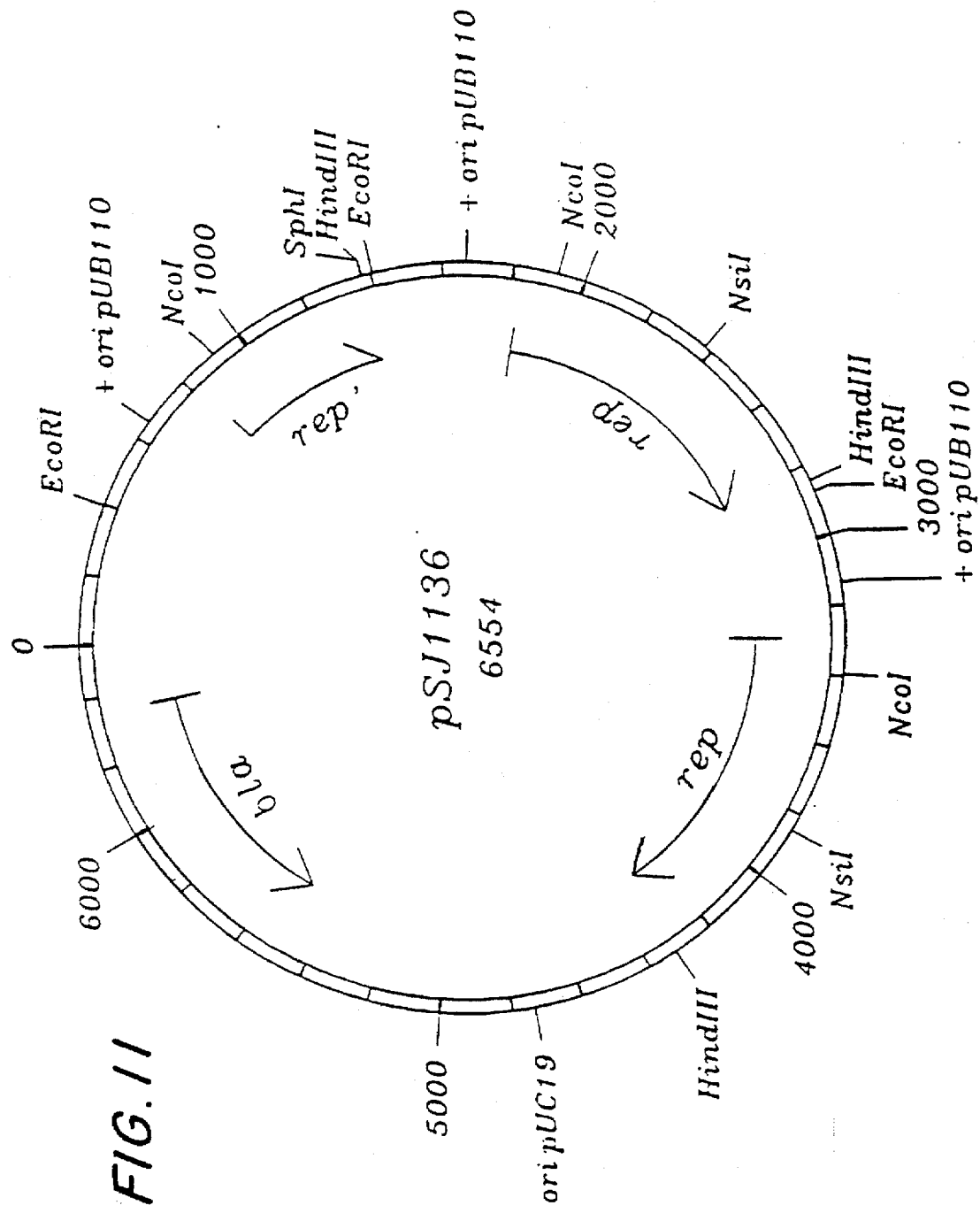
FIG. 11 shows a restriction map of plasmid pSJ1136.
Figure 12:
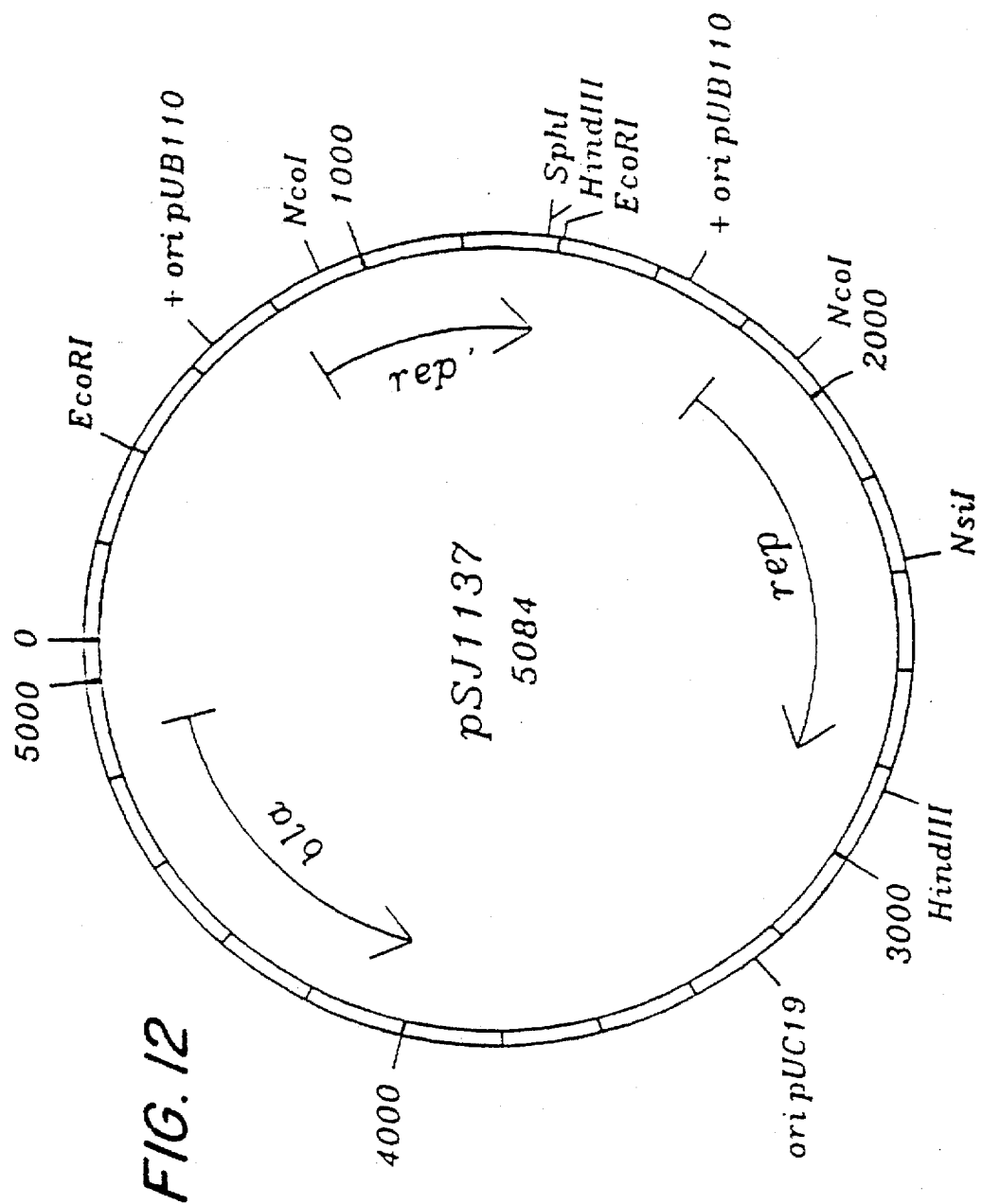
FIG. 12 shows a restriction map of plasmid pSJ1137.

A 1.4 kb HindIII fragment from pDN3060 (FIG. 6) containing the plus-origin followed by the intact rep gene was then inserted into the unique HindIII site of pSJ1130 (FIG. 10), and the ligated plasmid was transformed into E.coli SJ6, resulting in pSJ1136 (FIG. 11). In this experiment, the fragment happened to be inserted into pSJ1136 in two tandem copies. One of these copies was subsequently deleted by digestion of pSJ1136 with NsiI, religation of the 5.1 kb fragment and transformation of E. coli SJ6, resulting in pSJ1137 (FIG. 12) which contains one pUB110 origin next to a truncated rep gene and one pUB110 origin next to an intact rep gene.

Figure 14:
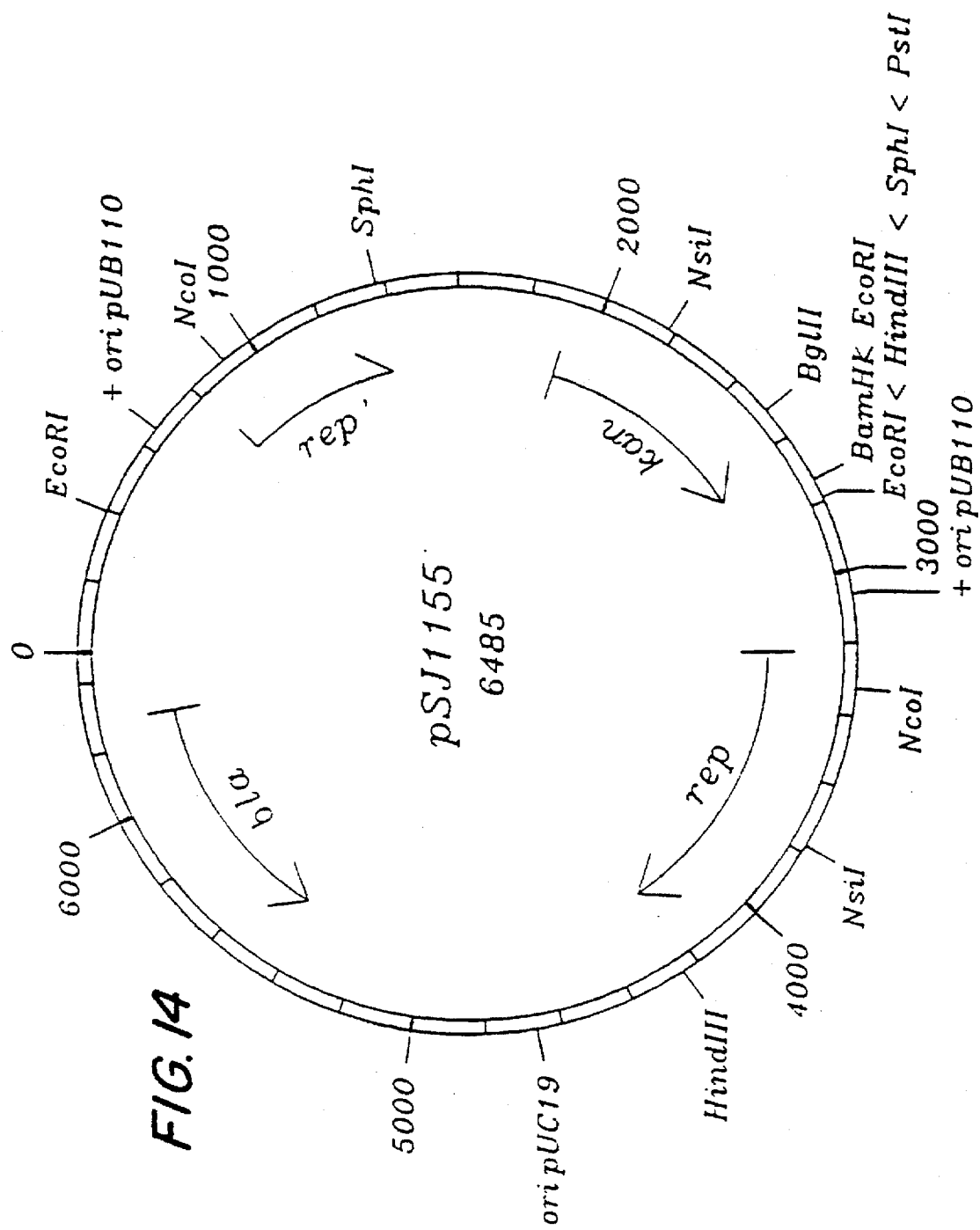
FIG. 14 shows a restriction map of plasmid pSJ1155.

The gene encoding kanamycin resistance (kan) was excised from plasmid pPL1484 (FIG. 13) on a 1.4 kb SphI fragment and inserted in each of the two possible orientations into the SphI site of pSJ1137 (FIG. 12), followed by transformation of E. coli SJ6, resulting in pSJ1155 (FIG. 14) and pSJ1157 (FIG. 15), respectively. pSJ1157 contained the kan gene in two tandem copies. One copy was excised with BamHI, and the 6.5 kb fragment religated and transformed into E. coli SJ6 to form pSJ1259 (FIG. 16).

Figure 18:
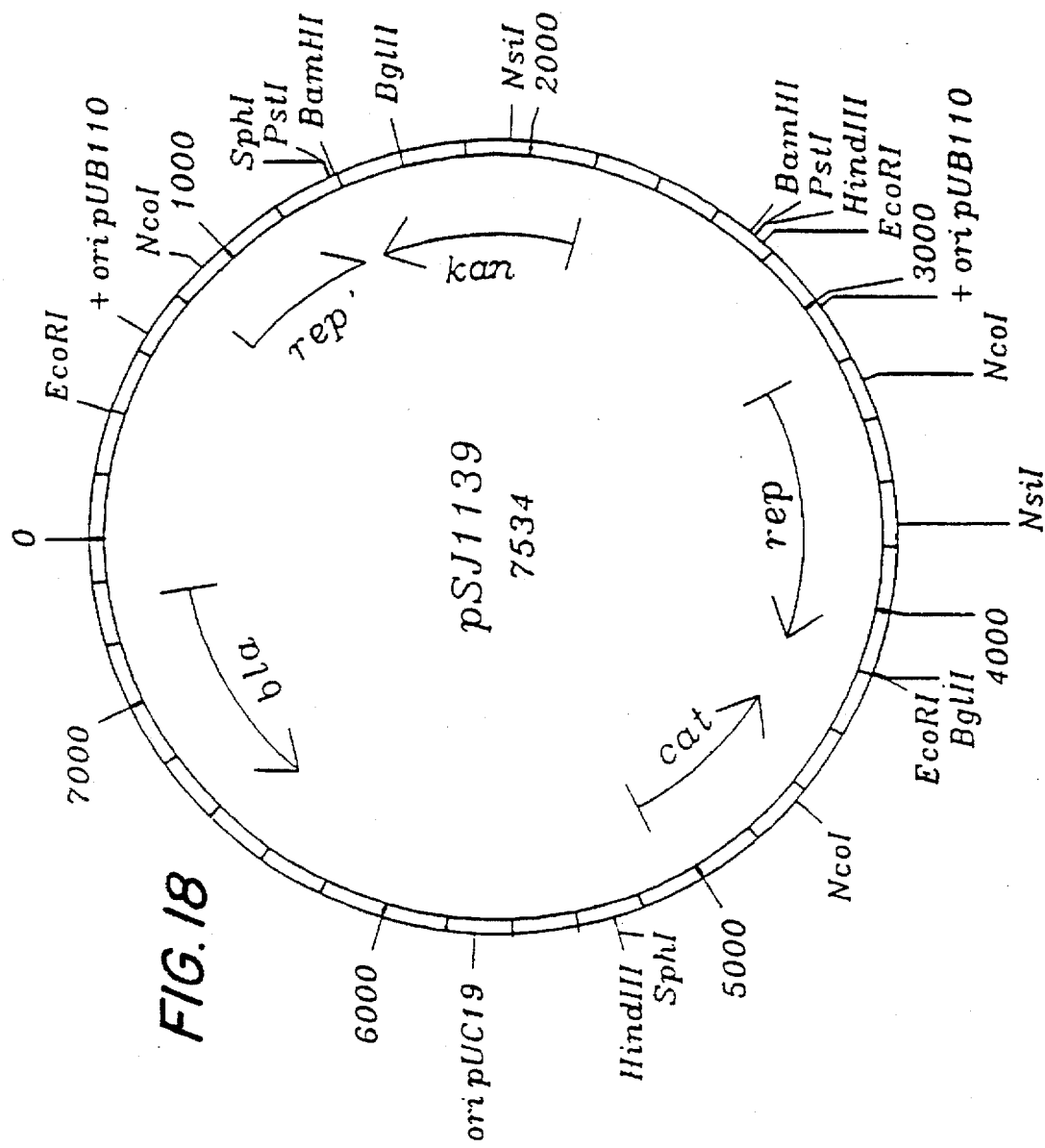
FIG. 18 shows a restriction map of plasmid pSJ1139.

Plasmid pSJ1139(FIG. 18) was constructed in the following way: The Bacillus plasmid pDN2904 (FIG. 17), containing a chloramphenicol resistance gene (cat), a kanamycin resistance gene (kan) and the pUB110 plus-origin with the corresponding rep gene was digested with SphI and ligated to pSJ1130 (FIG. 10) which had also been digested with SphI. The resulting plasmid pSJ1139 contains a pUB110 origin associated with a truncated rep gene and a pUB110 origin associated with an intact red gene.

EXAMPLE 3

Figure 19:
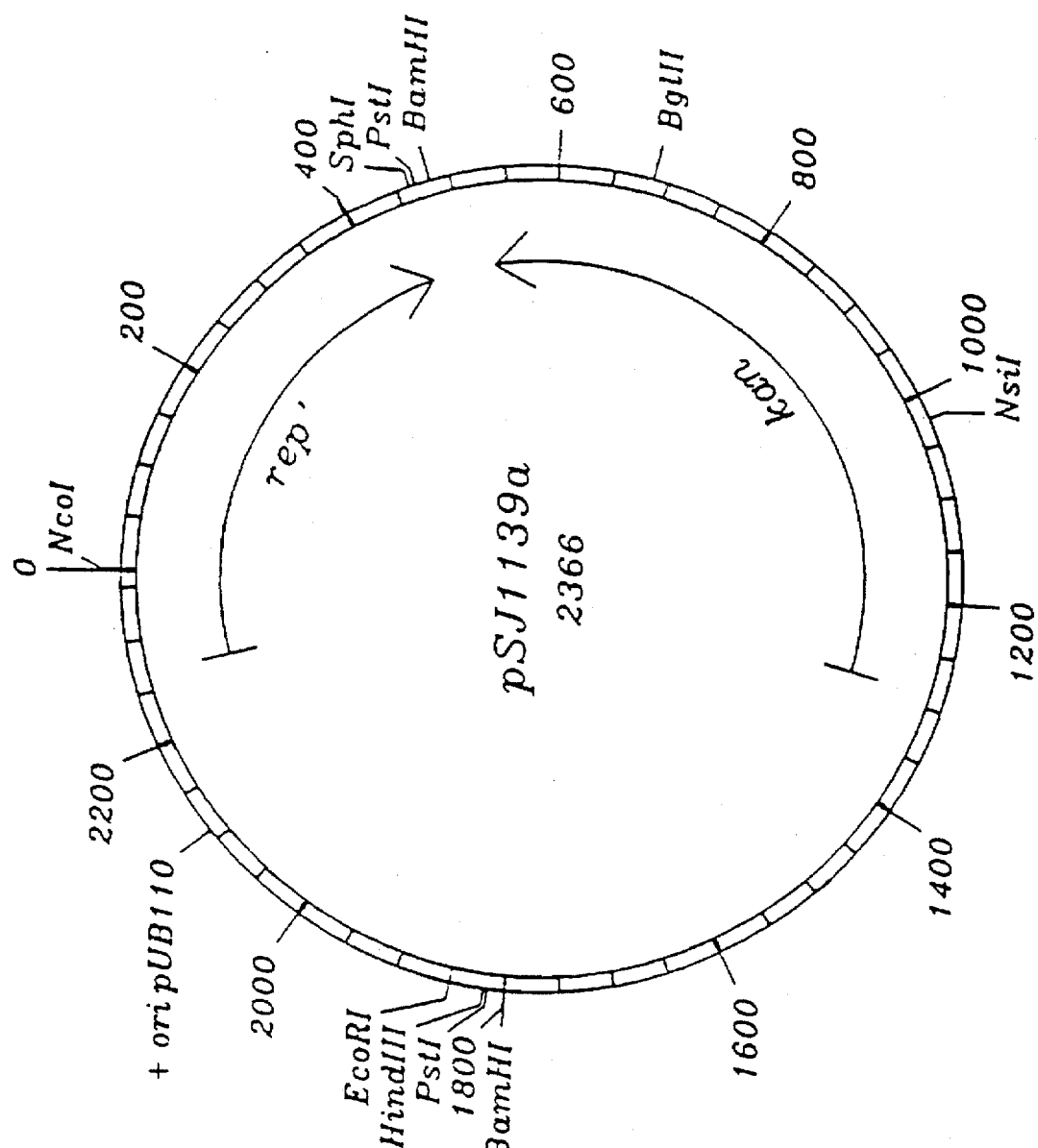
FIG. 19 shows a restriction map of plasmid pSJ1139a,
FIG. 20 shows a restriction map of plasmid pSJ1139b.
Figure 20:
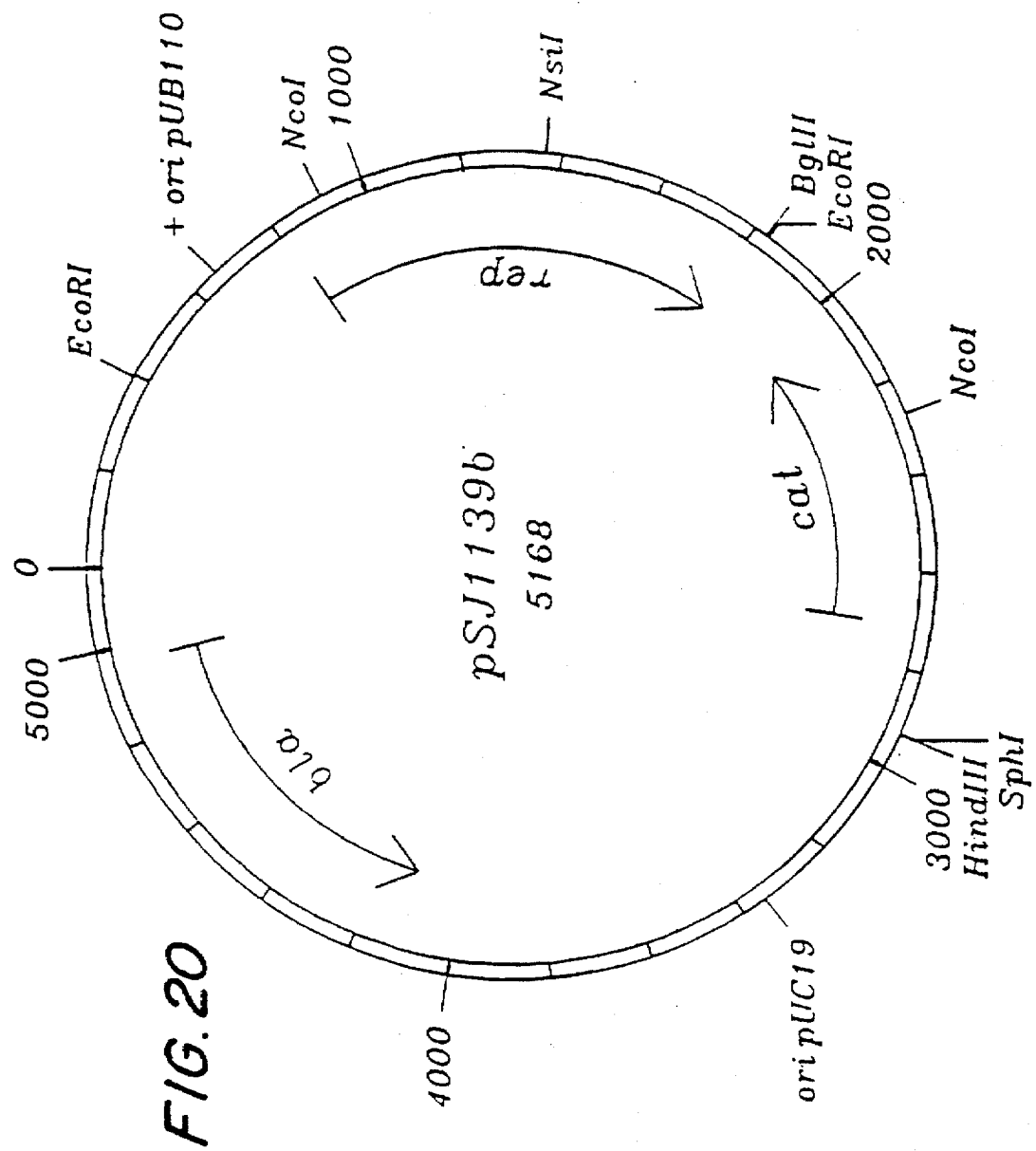

Formation of progeny DNA vectors from plasmids containing two pUB110 origins of replication in Bacillus subtilis Plasmid pSJ1139 (FIG. 18) (prepared from E. coli SJ1139 in a manner known per se) was transformed into B. subtilis DN1885 selecting for kanamycin resistance (10 μg/ml), and plasmid DNA was prepared from several transformants. Agarose gel electrophoresis of these plasmids, whether undigested or digested with a variety of restriction enzymes, showed the presence of two smaller DNA molecules of 5.1 kb and 2.4 kb, respectively, as well as a small amount of the full-length plasmid pSJ1139 of 7.5 kb. The restriction patterns obtained were the expected ones for formation of the two progeny vectors pSJ1139a (FIG. 19) and pSJ1139b (FIG. 20), either by homologous crossing-over between the two rep-sequences on pSJ1139 or by the action of the Rep protein which produces a nick at the pUB110 plus-origin in the plus DNA strand which is then displaced and recircularized as described in A. Gruss and S. D. Erlich, op. cit. (both these mechanisms could lead to the same two progeny vectors.

These vectors were further analyzed by retransformation into B. subtilis strain DN1885, and plating on LB plates containing either 10 μg/ml kanamycin or 6 μg/ml chloramphenicol, followed by replica plating of each plate onto a new plate containing the other antibiotic. Vectors were then isolated from each type of transformant and analyzed by agarose gel electrophoresis with the following results:

Transformants resistant to both chloramphenicol and kanamycin contain all three vector species(pSJ1139 of 7.5 kb, pSJ1139a of 2.4 kb and pSJ1139b of 5.1 kb). Transformants resistant to chloramphenicol and sensitive to kanamycin only contain pSJ1139b. Transformants resistant to kanamycin but sensitive to chloramphenicol were not obtained. The small progeny vector pSJ1139a of 2.4 kb is thus not able to replicate autonomously in B. subtilis.

EXAMPLE 4

Figure 21:
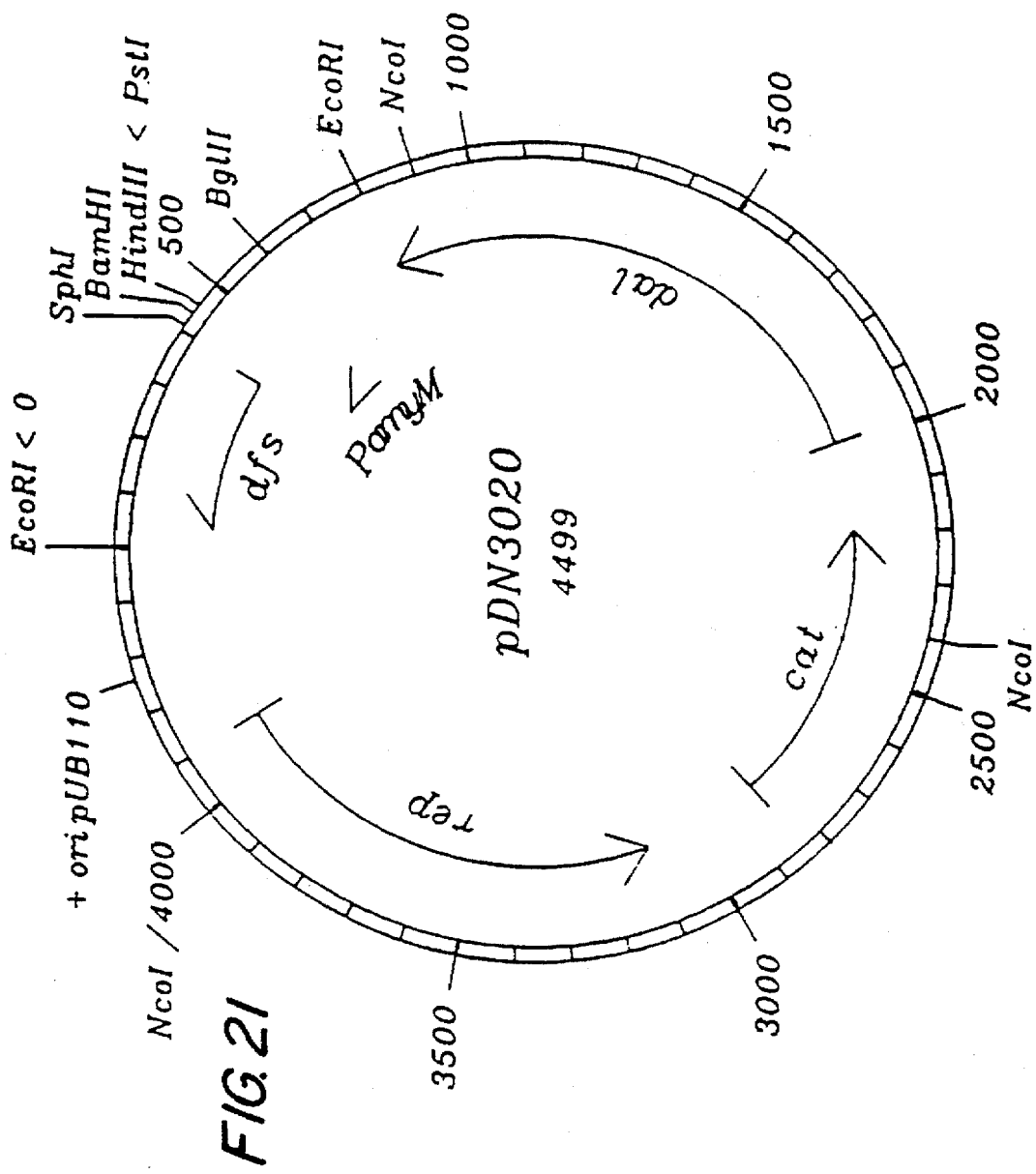
FIG. 21 shows a restriction map of plasmid pdn3020.
Figure 23:
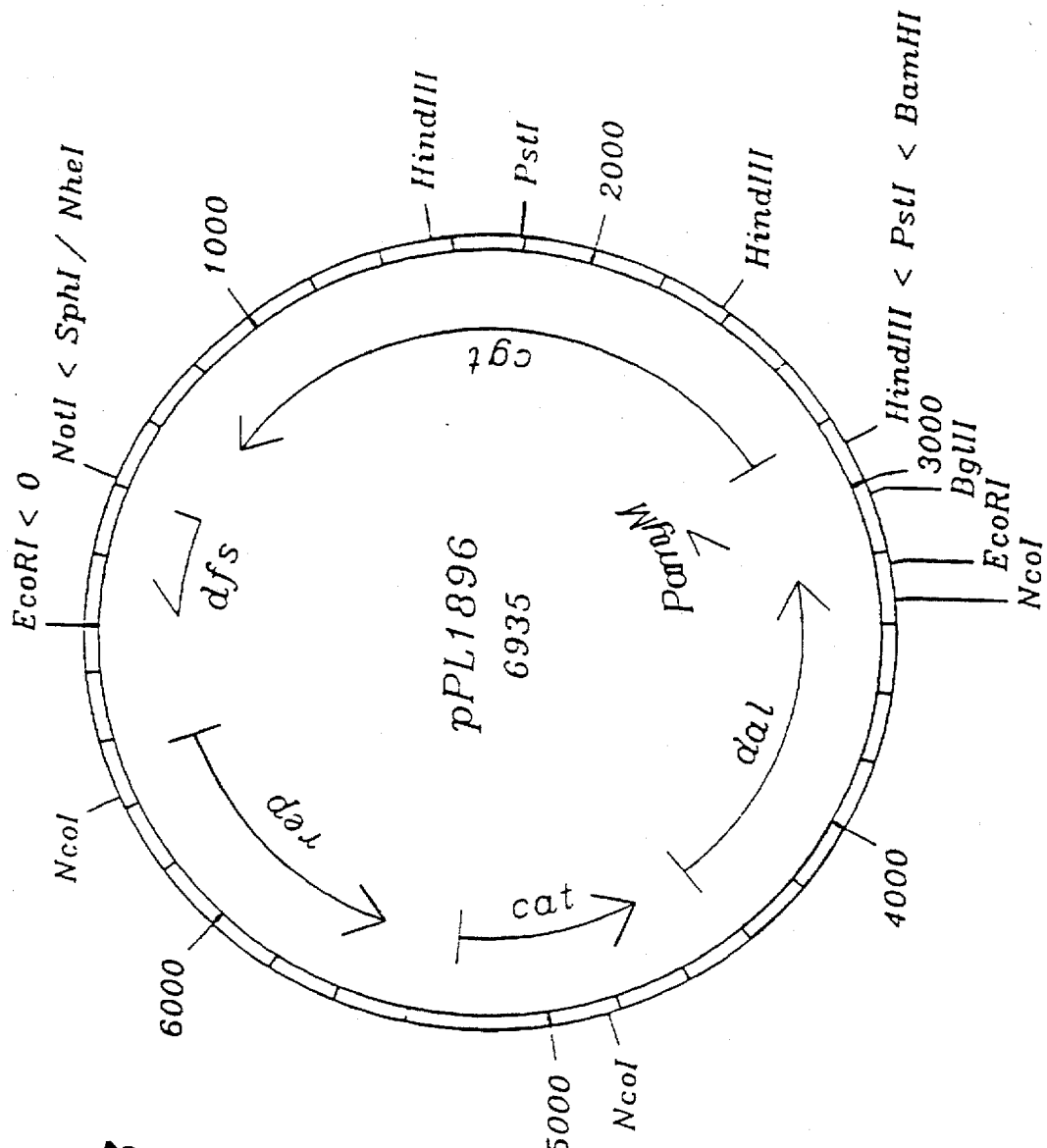
FIG. 23 shows a restriction map of plasmid pPL1896.

Stable integration of a non-replicative DNA molecule in the B. subtilis chromosome Construction of a B. subtilis strain containing one chromosomal copy of a cyclodextrin glycosyl transferase (CGTase) gene The CGTase gene (CGT) was excised from plasmid pPL1878 (FIG. 22) on a 2.5 kb BamHI-SphI fragment and ligated to the BamHI-SphI digested plasmid pDN3020 (FIG. 21) to form plasmid pPL1896 (FIG. 23). pDN3020 is a derivative of pDN1313 (Diderichsen, 1986), constructed by inserting a synthetic SphI-containing oligonucleotide linker (prepared as described in Example 1 above) into the EcoRI site of plasmid pDN1380 (Diderichsen and Christiansen, 1988) resulting in plasmid pDN1620. The promoter region from a maltogenic amylase from B. stearothermophilus (PamyM), present on pDN1620 (B. Diderichsen and L. Christiansen, op. cit.) was then transferred to SphI-BamHI digested pUC19 on an approximately 200 bp BamHI-SphI fragment resulting in plasmid pDN2977. The promoter region was excised from pDN2977 on an approximately 200 bp BglII-SacI fragment which was inserted into the polylinker region of pDN1313, thereby generating plasmid pDN3020. The CGTase gene on pPL1896 is flanked by two fragments of *B. subtilis* chromosomal DNA indicated as dal and dfs in FIG. 23. dal is the gene encoding D,L-alanine racemase of *B. subtilis* (Diderichsen 1986).

Plasmid pPL1896 was transformed into *B. subtilis* strain DN1686. When selecting solely for Dal$^+$ transformants, several strains were obtained that were chloramphenicol sensitive, CGTase$^+$. They were formed by a double homologous crossing-over between pPL1896 and the DN1686 chromosome, as described in Diderichsen, 1986. One such strain is PL1897, containing a chromosomally integrated copy of the CGTase gene.

Construction of an integration vector containing the CGTase gene

Figure 24:
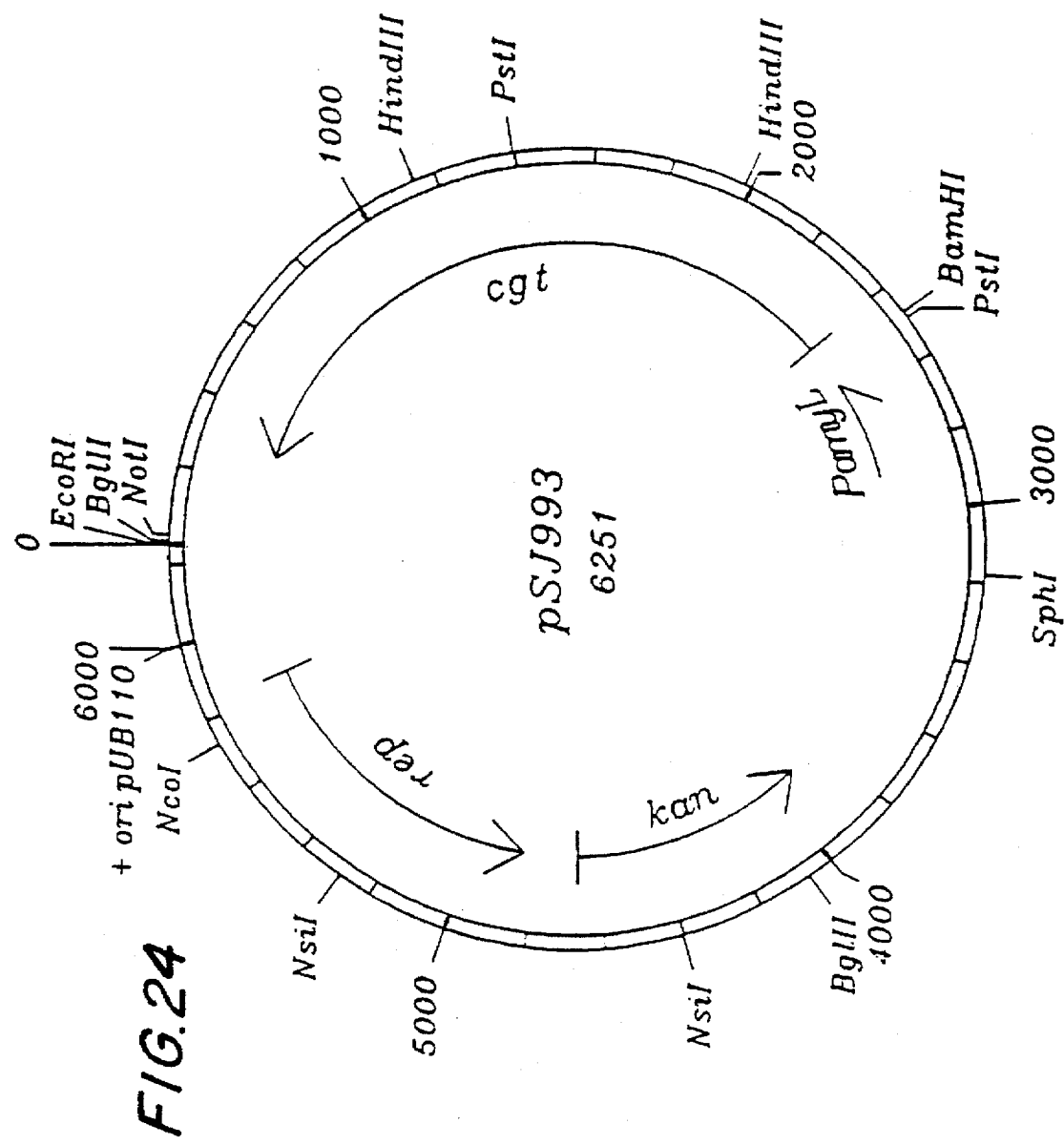
FIG. 24 shows a restriction map of plasmid pSJ993.

The CGTase gene was excised from pPL1878 (FIG. 22) on a 2.5 kb BamHI-NotI fragment. An expression vector was constructed by inserting a 0.6 kb SphI-PstI fragment containing the promoter region of the alpha-amylase gene cloned from an amylase-overproducing derivative of *B. licheniformis* ATCC9789 obtained by conventional mutagenesis procedures into a pUB110 derived vector containing the pUB110 origin and the gene encoding kanamycin resistance. The CGTase gene (cgt) was inserted downstream of this promoter between the BamHI and NotI sites, resulting in pSJ993 (FIG. 24).

Figure 25:
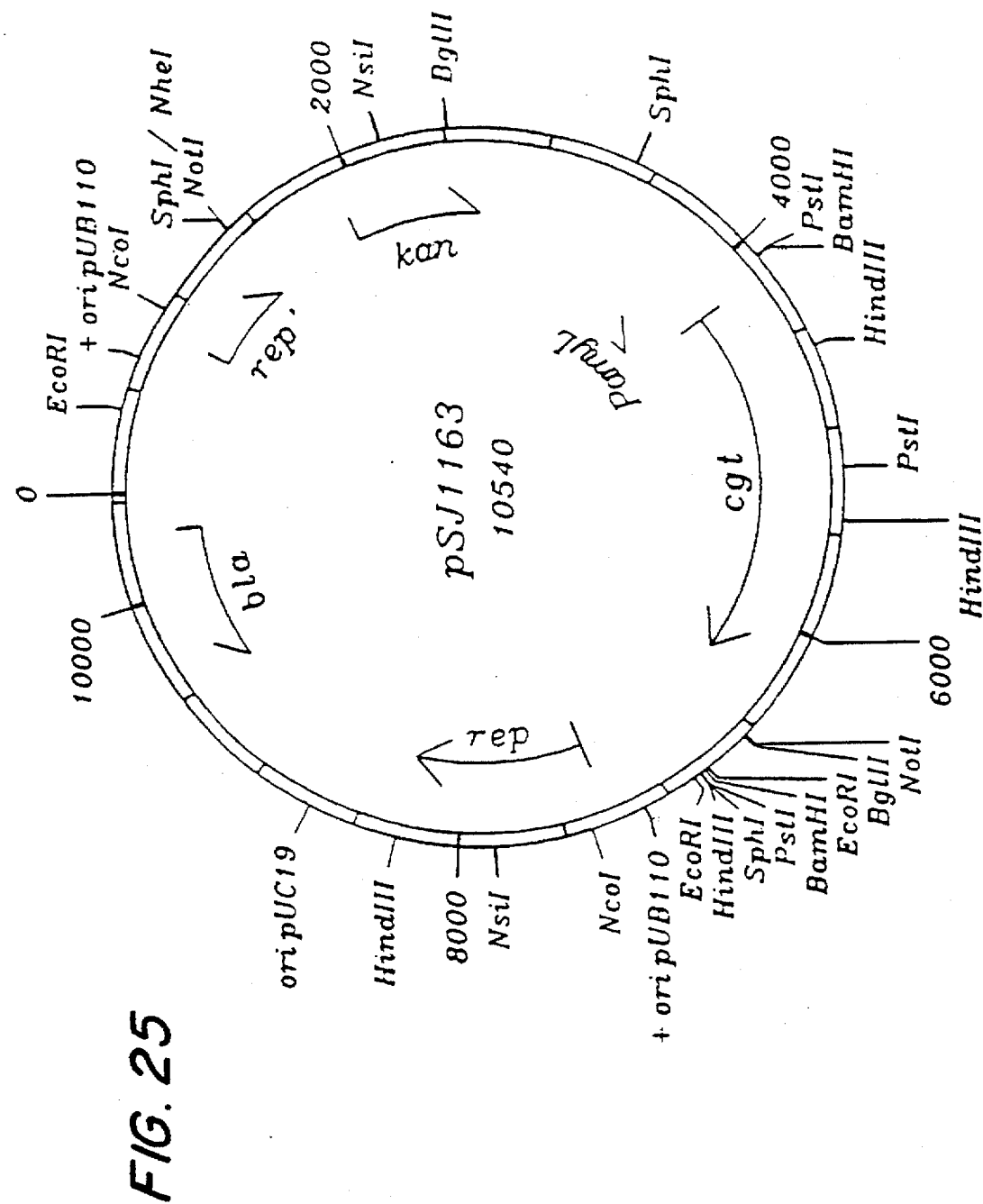
FIG. 25 shows a restriction map of plasmid pSJ1163.

A 4 kb BglII fragment from pSJ993 was inserted into the BglII site of pSJ1155 (described in Example 1 above, FIG. 14), the resulting plasmid was transformed into *E. coli* strain SJ6, and ampicillin-resistant, CGTase-producing transformants of *E. coli* SJ6 were isolated by plating transformants on LB plates containing 100 µg/ml ampicillin and 0.5% soluble starch, screening for the formation of a clear halo around the colonies after staining the plates with iodine vapour. A transformant harbouring the plasmid pSJ1163 (FIG. 25) in which the kanamycin resistance gene had been regenerated was kept for further experiments.

Figure 26:
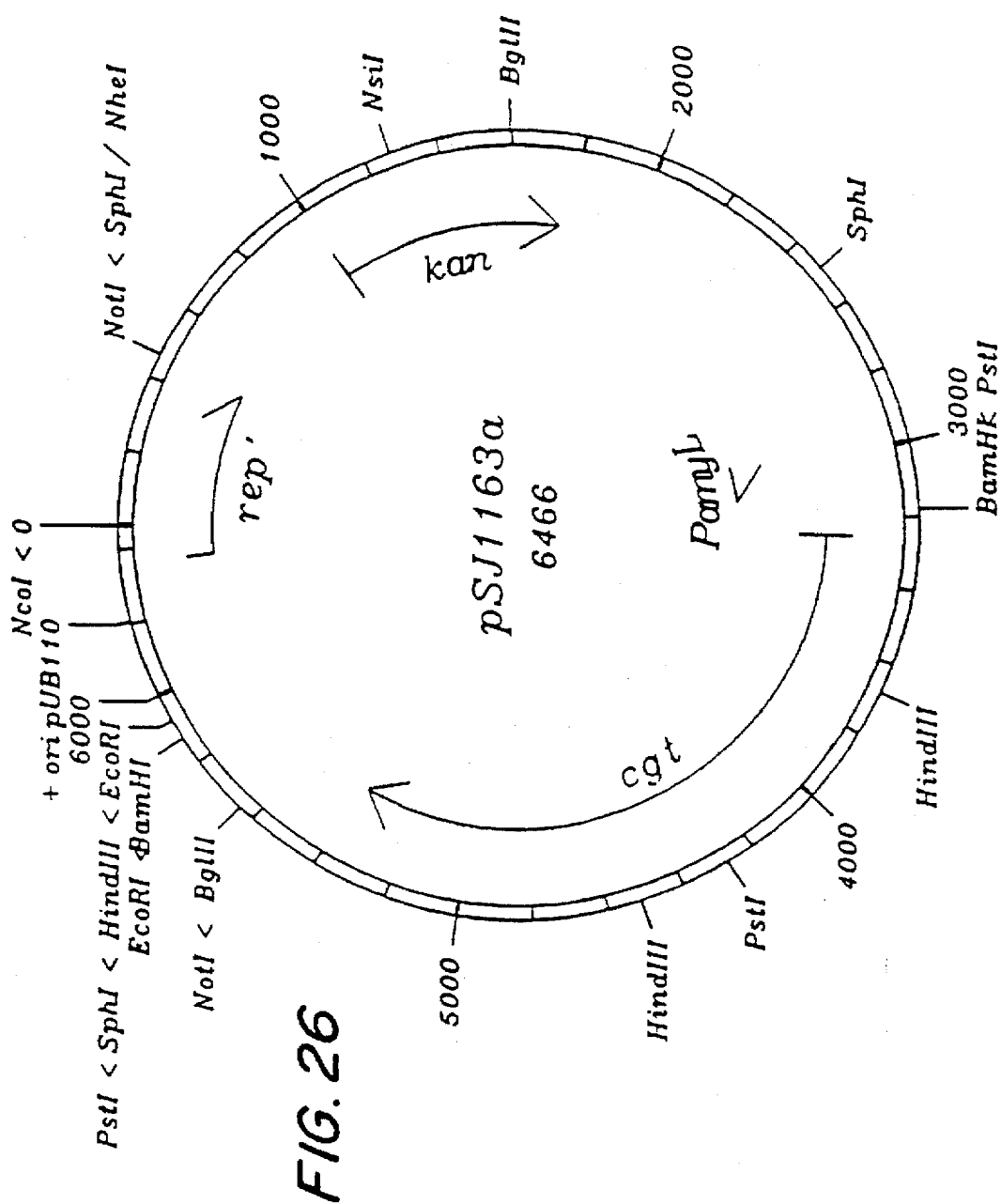
FIG. 26 shows a restriction map of plasmid pSJ1136a,
FIG. 27 shows a restriction map of plasmid pSJ1163b.
Figure 27:
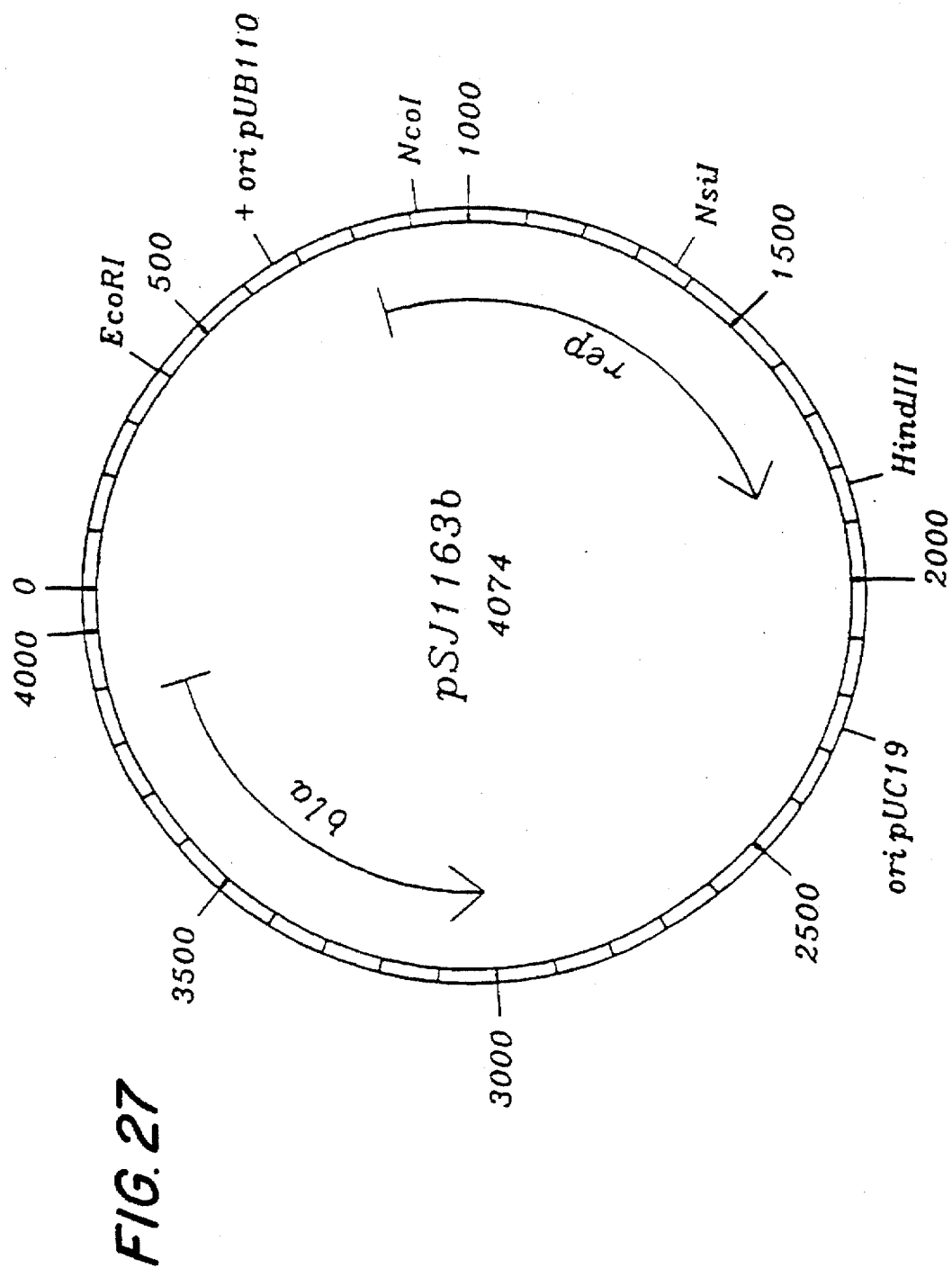

Formation of progeny vectors from pSJ1163 in *B. subtilis* strains DN1885 and PL1897 pSJ1163 (FIG. 25) was transformed into DN1885 and vector DNA was prepared from kanamycin-resistant transformants and analyzed by agarose gel electrophoresis. This showed traces of a 10.5 kb plasmid molecule, corresponding to pSJ1163, and two progeny vector molecules pSJ1163b of 4.1 kb (FIG. 27) and pSJ1163a of 6.4 kb (FIG. 26) in approximately equal and in far larger amounts, respectively, corresponding to progeny vectors derived either by homologous recombination between the two rep-sequences of pSJ1163 or by the action of the Rep protein at each plus origin in rolling circle replication as described above. The formation of progeny vectors as described above was also observed when pSJ1163 was transformed into PL1897, and two such transformants were kept for further experiments as strains SJ1168 and SJ1170.

Isolation of integrants containing non-replicative DNA molecules

Strains SJ1168 and SJ1170 were inoculated into 10 ml TY medium containing 5 µg/ml kanamycin and incubated overnight at 37° C. 100 µl of each culture were then inoculated into fresh TY medium and the incubation was repeated. After four such cycles of incubation overnight, plasmid DNA was prepared from the two cultures and analyzed by agarose gel electrophoresis. No plasmid molecules were observed. When the plasmid preparation was used to transform *E. coli* selecting for ampicillin resistance, no transformants were obtained, indicating that neither the original 10.5 kb pSJ1163 nor the 4.1 kb progeny vector molecule pSJ1163b were present. The kanamycin-resistant, plasmid-free strains were kept for further experiments as SJ1223 and SJ1237.

Amplification of integrated DNA

By selecting for growth in TY medium containing gradually increasing concentrations of kanamycin, strains were isolated that were able to grow in 20, 50, 100, 200, 400, 600, 800, 1000, 1200, and 1400 µg/ml kanamycin. In chromosomal DNA from strains resistant to above about 400 ug/ml kanamycin, digestions with NheI or NotI revealed a DNA band of the size expected from digestion of the 6.4 kb progeny vector pSJ1163a with these enzymes. This band did not appear in digests of DNA prepared from strains with a lesser degree of kanamycin resistance. A conservative estimate would be that at least 5–10 copies of the integrated DNA were present when this band appeared.

Stability of integrated DNA

Strains resistant to 400 µg/ml kanamycin were grown for one week at 37° C. in shake flasks containing BPX medium without any added kanamycin. They were then plated onto LB plates and subsequently replica plated onto plates containing 10 µg/ml kanamycin. Of about 100 colonies, all were kanamycin resistant, indicating the stable inheritance of the kanamycin resistance gene present on the integrated DNA in the abscence of selection pressure.

Stability of a plasmid-borne CGTase gene in *B. subtilis*

Plasmid pP11892 is essentially identical to pSJ993 (FIG. 24), the only difference being that a different polylinker region is present downstream of the CGTase gene. This plasmid was introduced into DN1885 and the resulting strain SJ984 was grown for one week at 37° C. in shake flasks containing BPX medium without any added kanamycin. Plating on kanamycin-containing plates (10 µg/ml) gave a 10-fold lower cell count than plates without kanamycin, indicating that 90% of the cells had lost their plasmid. This was also reflected by the finding that less than 10% of the colonies on plates without kamamycin produced CGTase.

EXAMPLE 5

Formation of progeny vectors from pSJ1156 in *B. licheniformis* ATCC 9789.

Figure 15:
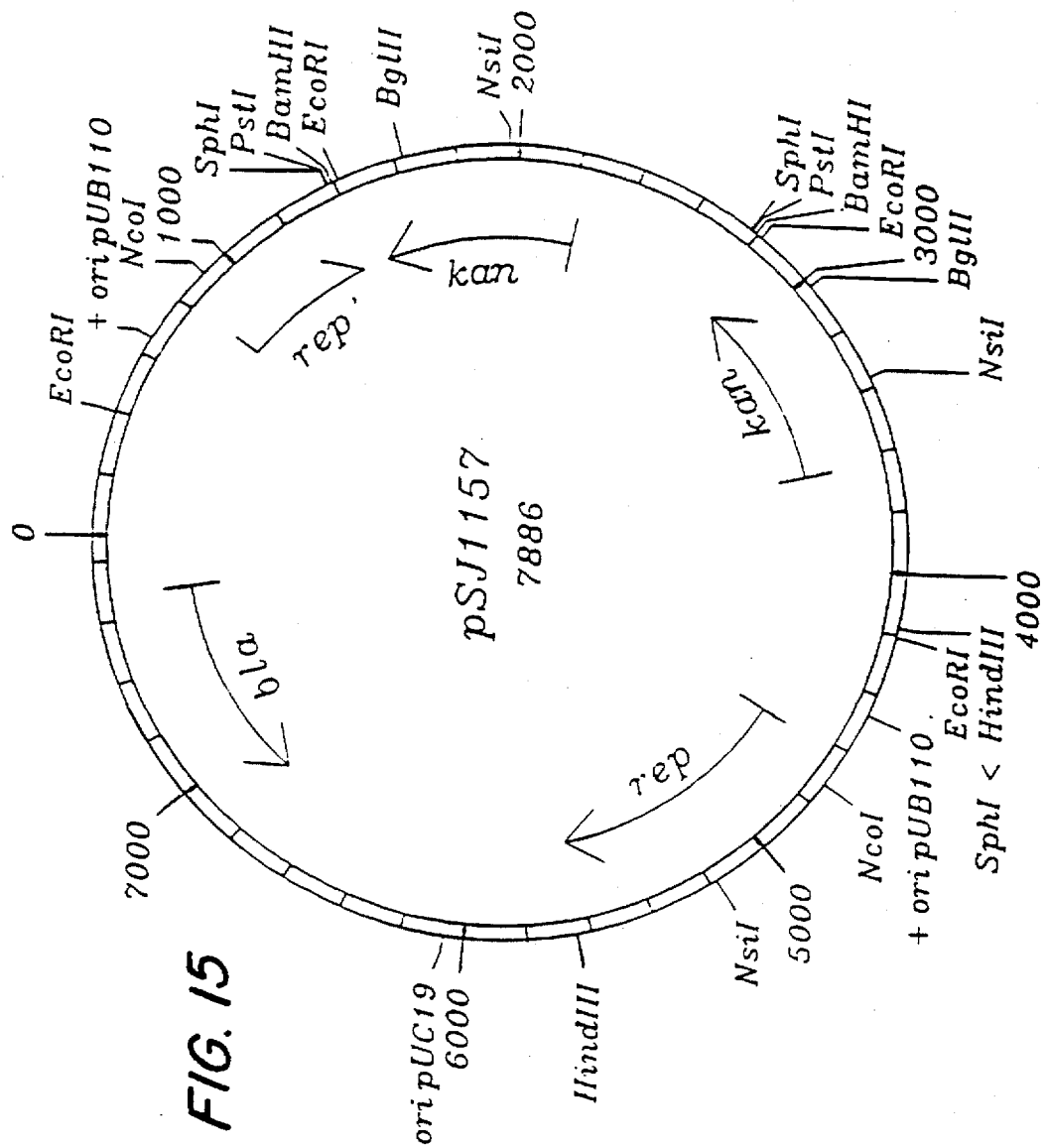
FIG. 15 shows a restriction map of plasmid pSJ1157.
Figure 16:
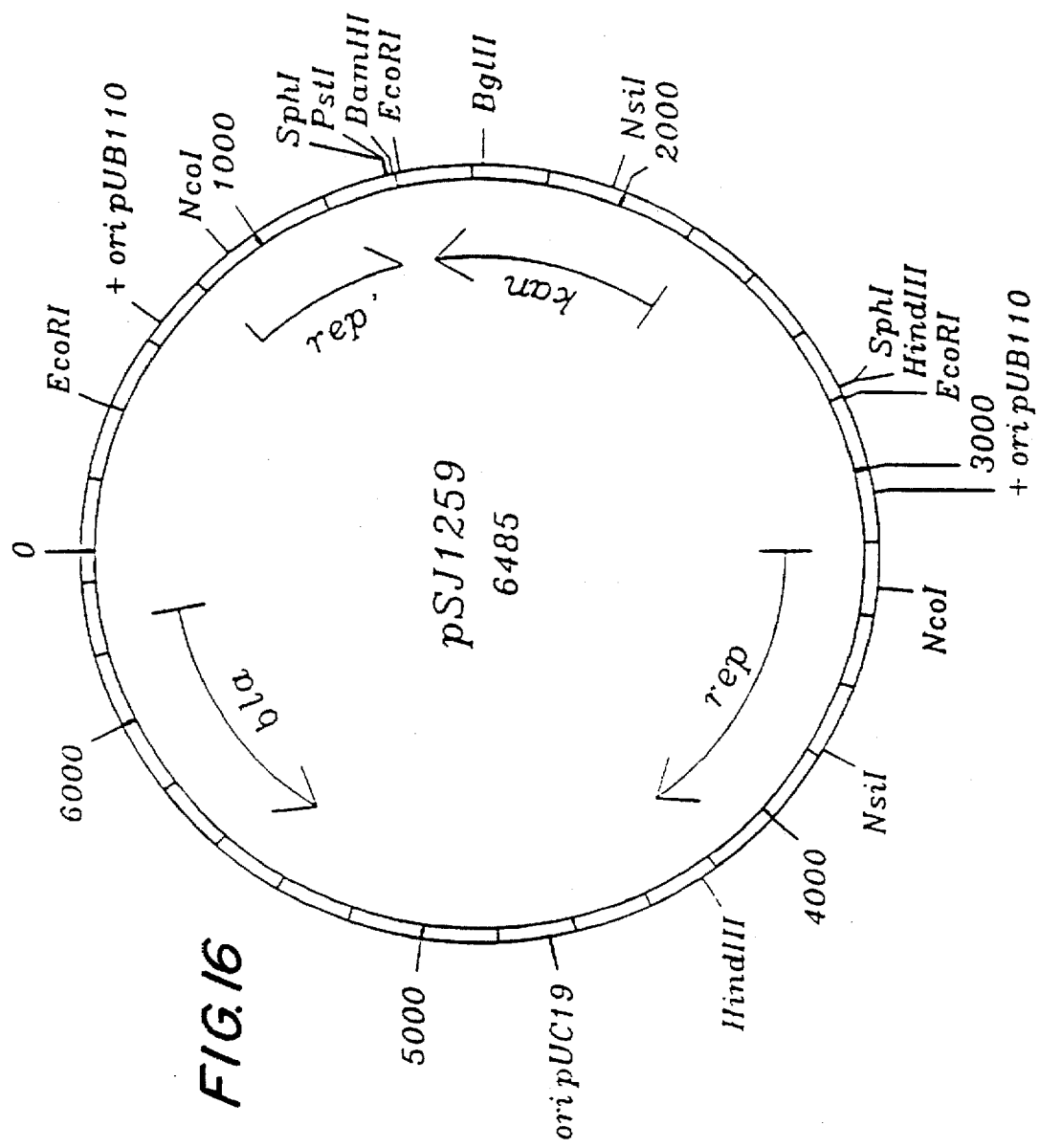
FIG. 16 shows a restriction map of plasmid pSJ1259.
Figure 28:
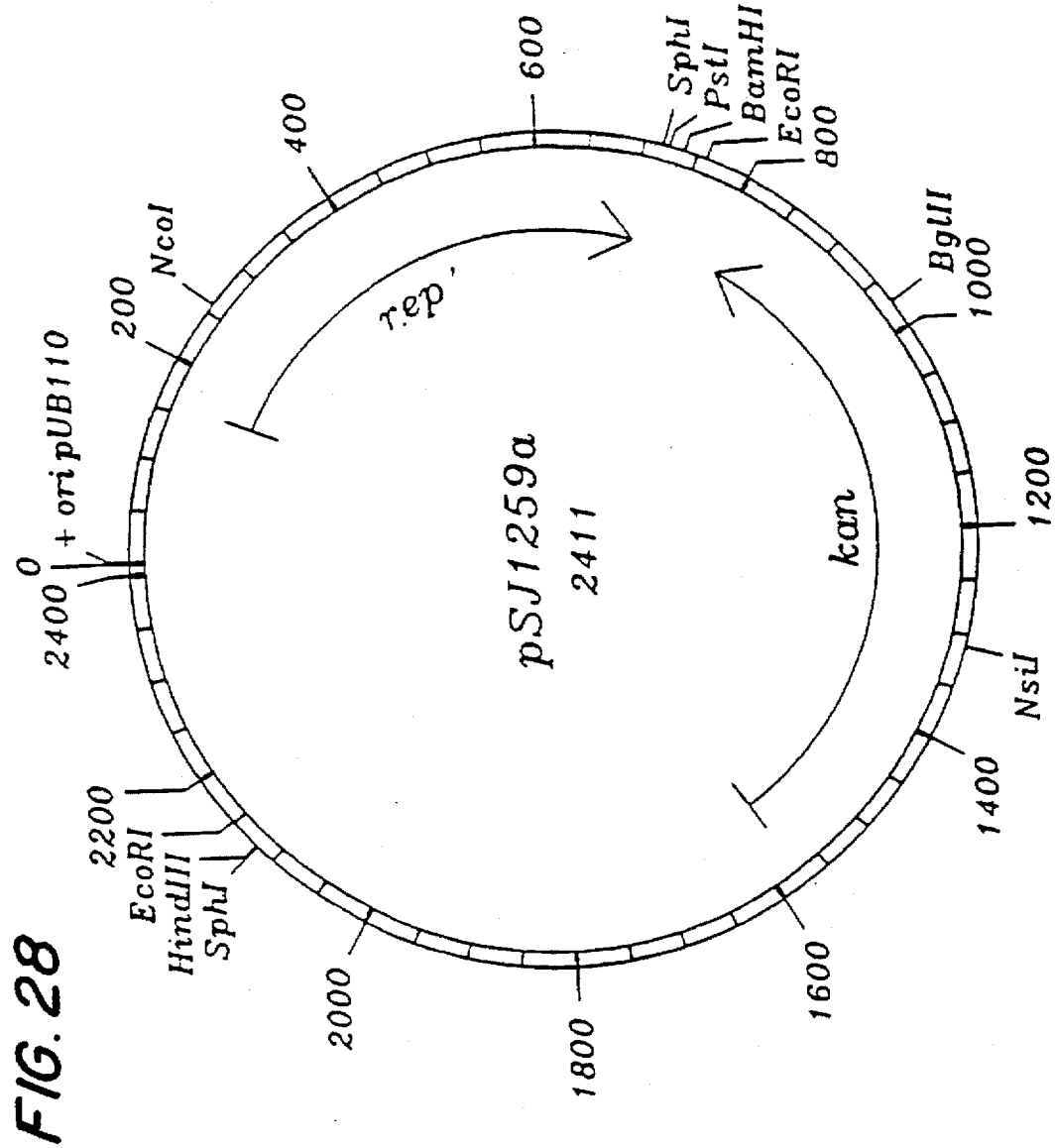

Plasmid pSJ1156 is identical to pSJ1157 shown in FIG. 15. pSJ1156 was introduced into *B. licheniformis* ATCC 9789 by protoplast transformation, selecting for kanamycin resistance, resulting in strain SJ1199. Analysis of the plasmid content of SJ1199 by restriction enzyme digestion and agarose gel electrophoresis revealed the presence of two plasmid molecules. One was identical to pSJ1259 (FIG. 16) and most likely formed by deletion of one copy of the kan gone by homologous recombination. The other corresponded to pSJ1259a (FIG. 28), one of the two progeny molecules that could be formed either by homologous recombination between the two rep sequences of pSJ1259 or by the action of the Rep protein at each plus origin in rolling circle replication as described above.

EXAMPLE 6

Figure 29:
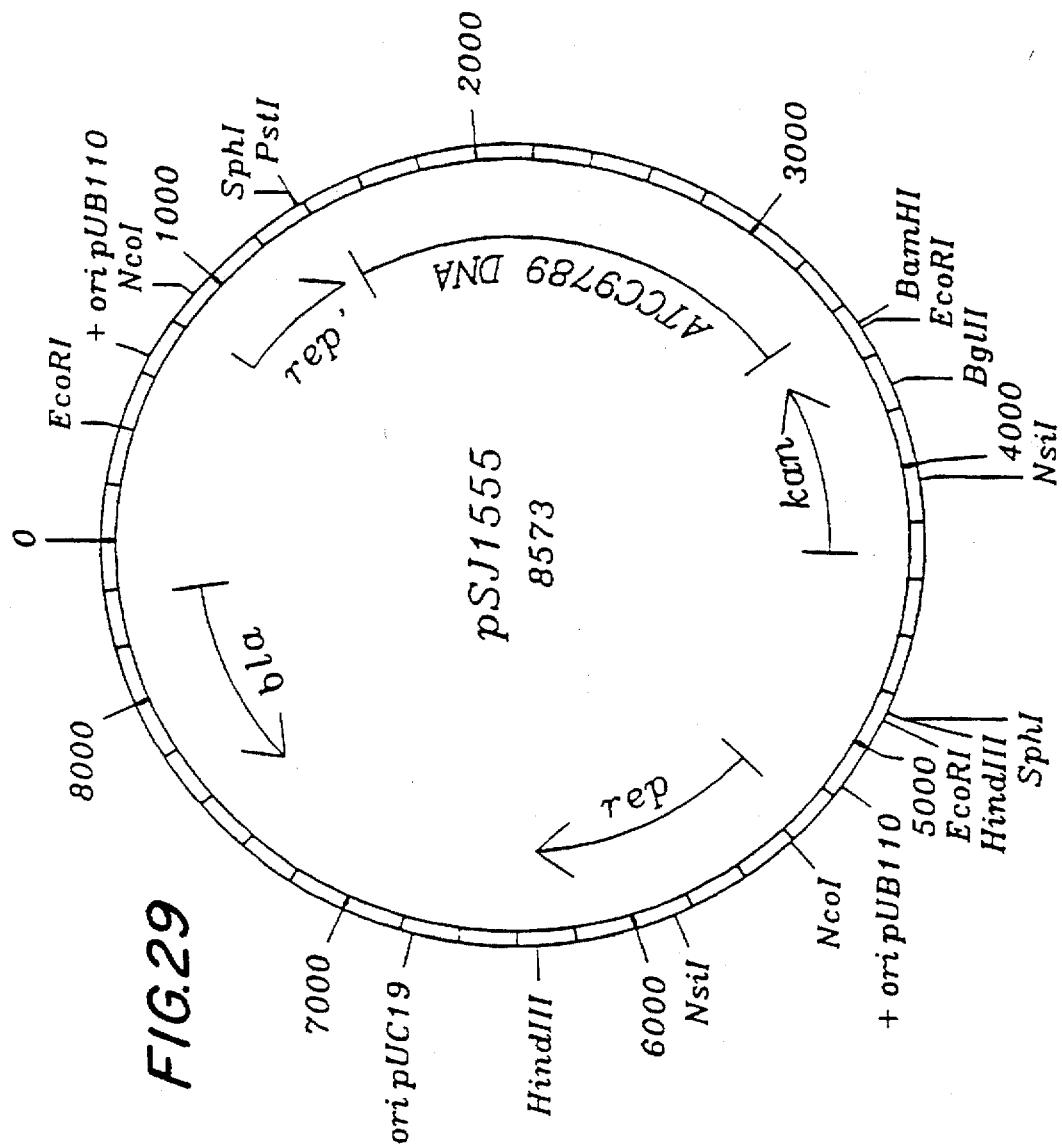
FIG. 29 shows a restriction map of plasmid pSJ1555.
Figure 30:
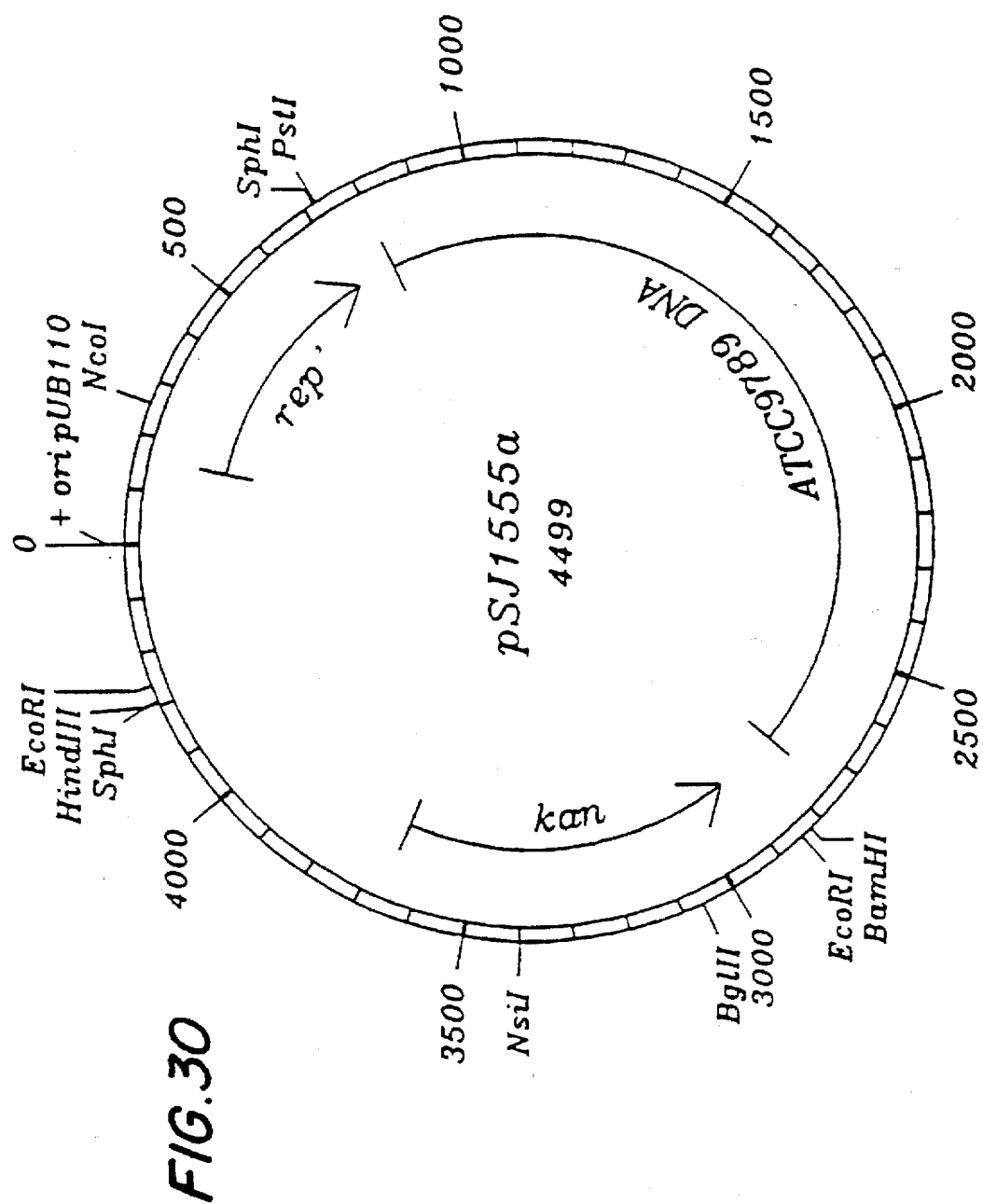
Figure 31:
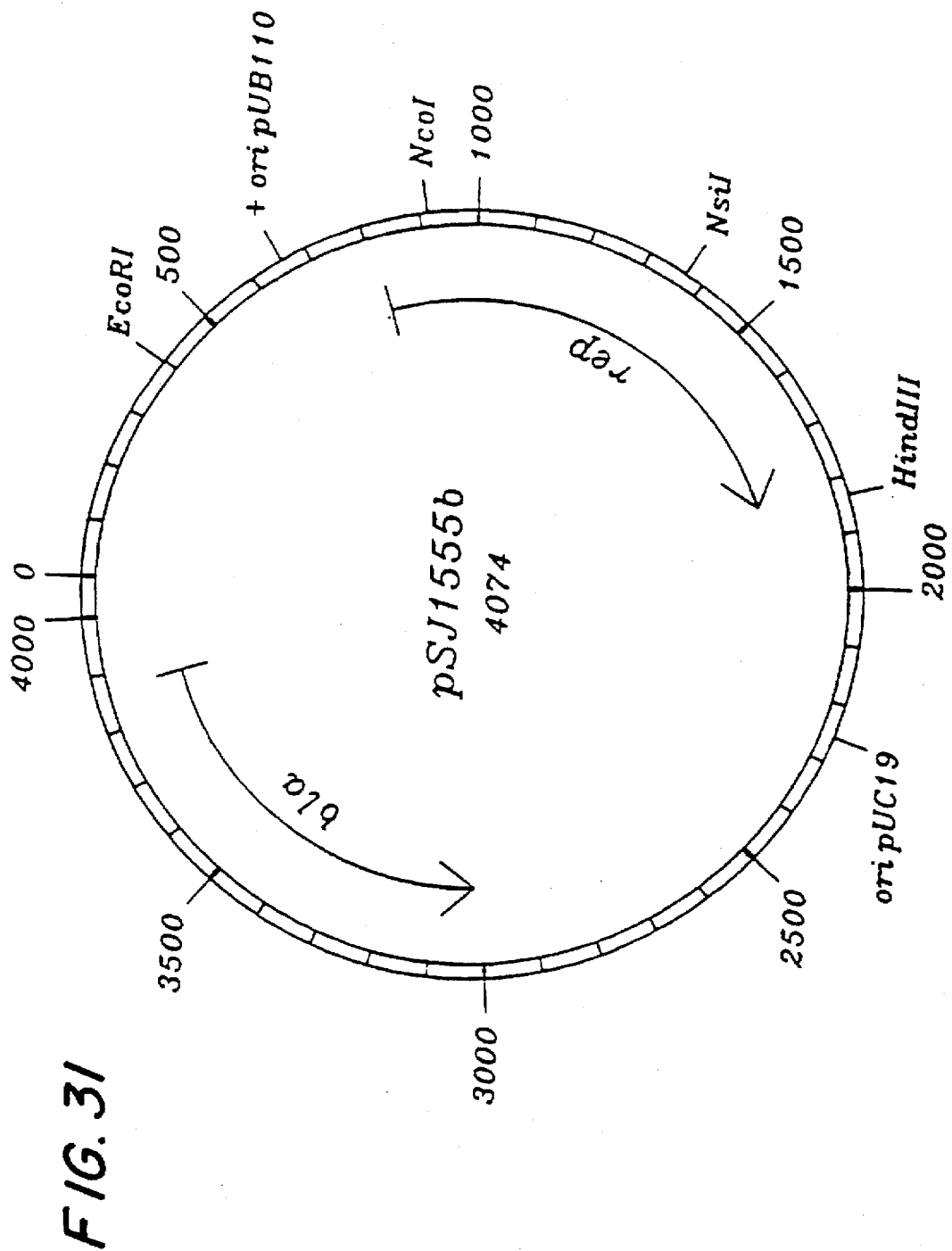
FIG. 31 shows a restriction map of plasmid pSJ1555b.
Figure 32A:
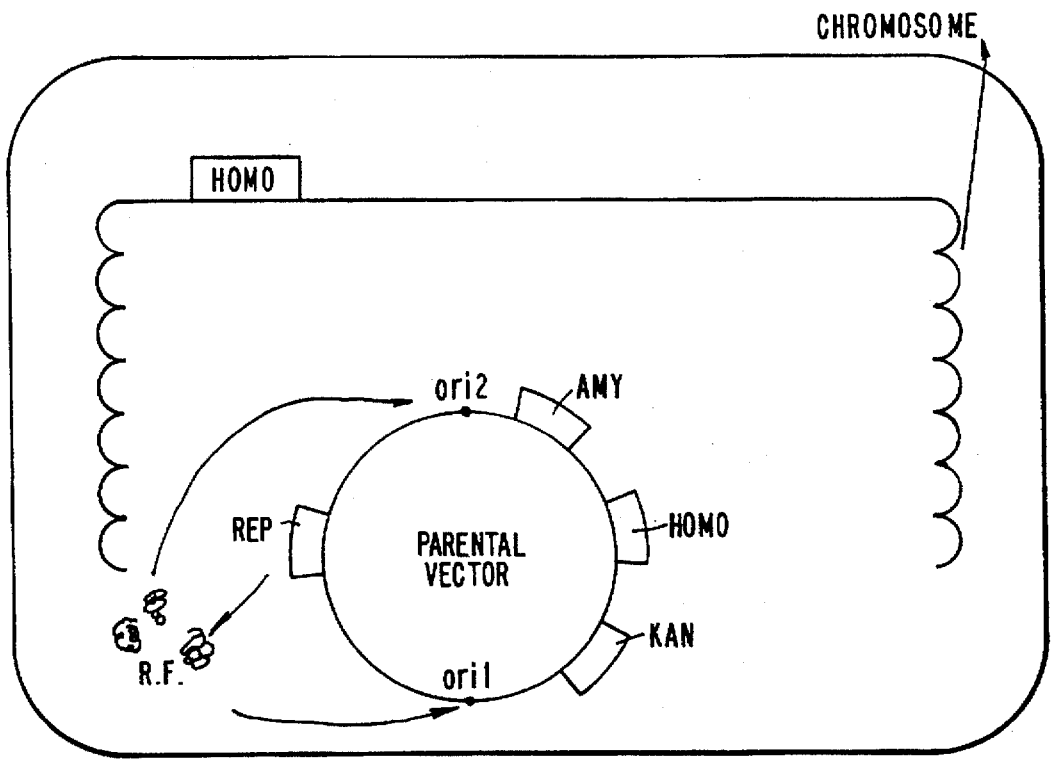
FIG. 32A shows a cell transformed with a single plasmid vector which has a first origin of plasmid replication (ori1) followed by the gene coding for the replication factor (rep), followed by a second origin of replication (ori2), a DNA sequence of interest (e.g. amy), and a selection marker (e.g. kan).
Figure 32B:
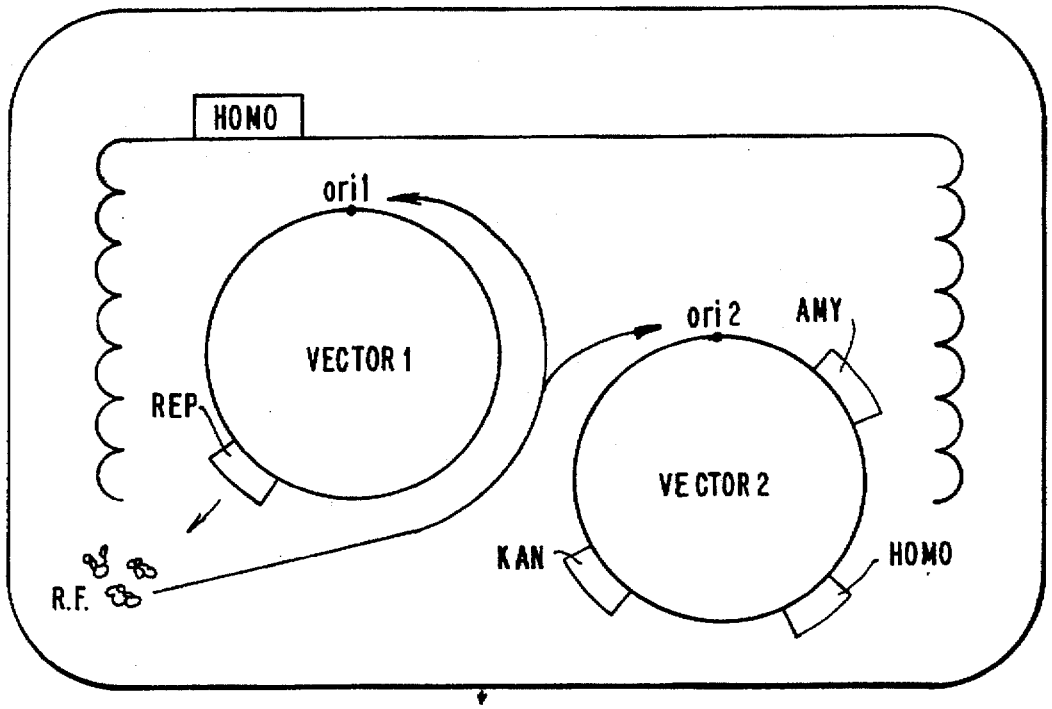
FIG. 32B shows the segregation of the plasmid of FIG. 32A on replication.
Figure 32C:
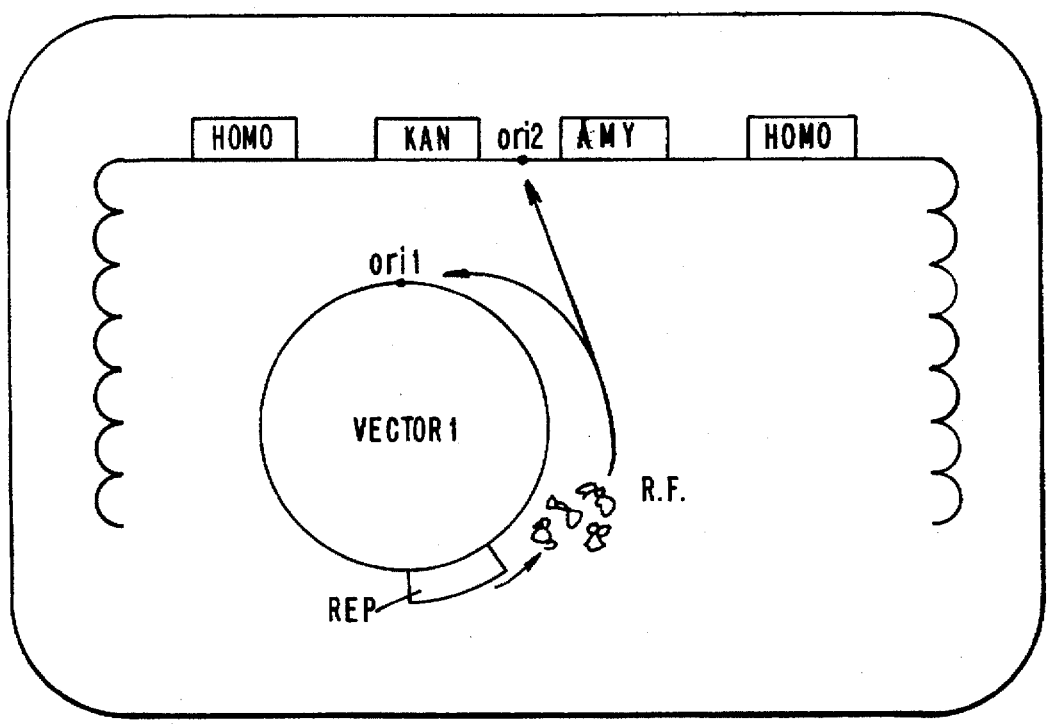
FIG. 32C shows the host cell containing the integrated DNA.
Figure 32D:
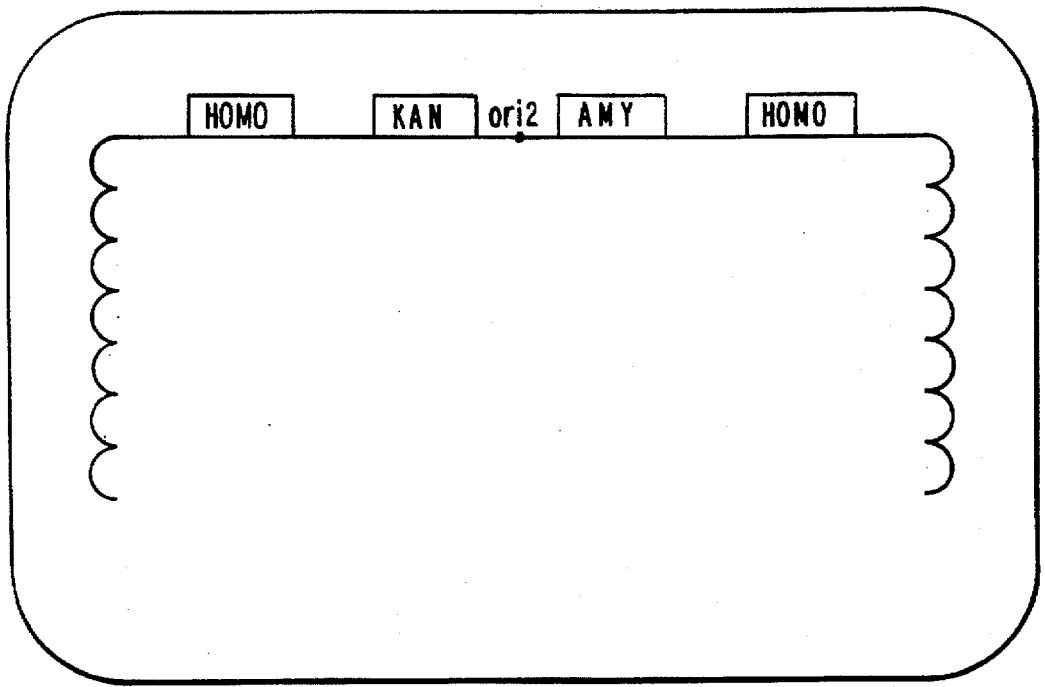
FIG. 32D shows the host cell containing the integrated DNA after selection with kanamycin.

Stable integration of a non-replicative DNA molecule in the *B. licheniformis* ATCC 9789 chromosome Construction of integration vector Plasmid pSJ1260 is identical to pSJ1259 shown in FIG. 16. Chromosomal DNA from *B. licheniformis* ATCC 9789 was digested with PstI+BamHI and fragments between 2 and 4 kb were isolated from an agarose gel. These fragments were ligated into pSJ1260 digested with PstI+BamHI, and transformed into *E. coli* SJ6 selecting ampicillin resistance. One transformant obtained contained an insert of 2.1 kb and the plasmid was denoted pSJ1555 (FIG. 29). *E. coli* SJ6 containing pSJ1555 was deposited at the National Collection of Industrial and Marine Bacteria Ltd, 23 St. Machar Drive, Aberdeen, AB2 1RY, Scotland, UK on Dec. 12, 1990 in accordance with the provisions of the Budapest Treaty on the International Recognition of the Deposit of Microorganisms for the Purpose of Patent Procedure, with the accession number NCIMB 40346. This plasmid has the capacity to form the two progeny molecules pSJ1555a (FIG. 30) and pSJ1555b (FIG. 31).

Isolation of *B. licheniformis* integrant containing a non-replicative DNA molecule.

pSJ1555 was introduced into *B. licheniformis* ATCC 9789 by protoplast transformation, selecting for kanamycin resistance. One regenerated, kanamycin-resistant transformant (SJ1613) was plasmid-free as seen by gel electrophoresis of a plasmid-preparation from that transformant, and the plasmid preparation was unable to transform *B. subtilis* to kanamycin resistance. This result indicates that the non-replicative progeny molecule pSJ1555a had formed and had been integrated into the ATCC 9789 chromosome.

Amplification and stability of integrated DNA

Strain SJ1613 was grown in successive 10 ml TY cultures containing kanamycin at 10, 20, 50, 100, 200, 400, 600, 800, 1000, 1500, 2000, 2500, 3000, 4000 and 5000 ug/ml, and strains growing at each of these different concentrations were kept for further study. Strains resistant to 20, 200 and 1500 ug/ml kanamycin were further analyzed. Chromosomal DNA from the two latter strains revealed upon digestion with BamHI a distinct band of 4.5 kb, absent from DNA of the first strain, as expected for strains containing multiple copies of pSJ1555a integrated in the chromosome.

All strains were grown in BPX shake flasks at 37° C. for 7 days without kanamycin, and then streaked on LB plates. Replica plating from LB plates to kanamycin plates (10 ug/ml) revealed no kanamycin sensitive colonies. Colony counts on plates with and without kanamycin (10 ug/ml) were obtained for the three strains resistant to 20, 200 and 1500 ug/ml kanamycin, and were in all cases $10^{10}$ ml$^{-1}$, indicating stability of the integrated kan gene.

REFERENCES

Akamatzu, T., Sekiguchi, J. (1984). An improved method of protoplast regeneration for Bacillus species and its application to protoplast fusion and transformation. Agric. Biol. Chem. 48, 651–655.

Yanisch-Perron, C., Vieira, J., Messing, J. (1985). Improved M13 phage cloning vectors and host strains: Nucleotide sequences of the M13mp18 and pUC19 vectors. Gene, 33, 103–119.

Diderichsen, B. (1986). A genetic system for stabilization of cloned genes in *Bacillus subtilis*. In Bacillus Molecular Genetics and Biotechnology Applications. Ganesan, A. T. and Hoch, J. A., Eds., pp. 35–46, Academic Press.

Diderichsen, B., Christiansen, L. (1988). Cloning of a maltogenic alpha-amylase from a *Bacillus stearothermophilus*. FEMS Microbiology Letters, 56, 53–60.

Diderichsen, B., Wedsted, U., Hedegaard, L., Jensen, B. R., Sjøholm, C. (1990). Cloning of aldB, which encodes α-acetolactate decarboxylase, an exoenzyme from Bacillus brevis. J. Bacteriol., 172, 4315–4321.

Gryczan et al. (1980). J. Bacteriol. 141, 246–253.

Gryczan et al. (1978). Characterization of *Staphylococcus aureus* plasmids introduced by transformation into *Bacillus subtilis*. J. Bacteriol. 134, pp. 318–329.

Mandel, A., Higa, A. (1970). J. Mol. Biol. 53, 159–162.

Starnes, R. L., Trackman, P. C., Katkocin, D. M. (1989). Thermostable cyclodextrin glycosyl transferase, its production and use. International Patent Application, Publication No. WO 89/03421.

Yasbin, R. E., Williams, G. A., Young, F. E. (1975). J. Bacteriol. 121, 296–304.

R. Villafane, D. H. Beckhofer, C. S. Narayanan and D. Dubnau.: Replication control genes of plasmid pE194. J. Bact.(1987), 169, p4822–4829.

S. Horinouchi and B. Weisblum.: Nucleotide sequence and functional map of pE194 a plasmid that specifies inducible resistance to macrolide lincosamide and Streptogramin type B antibiotics.: J.Bact.,(1982), p804–814.

Kieser, T. (1984). Factors affecting the isolation of CCC DNA from *Streptomyces lividans* and *Escherichia coli*. Plasmid 12, 19–36.

---

We claim:

1. A method of producing a bacterial cell which in its genome carries an integrated non-replicative DNA construct comprising (1) a DNA sequence of interest, (2) a DNA sequence which is homologous with a region of the genome of the cell, and (3) an origin of replication, the DNA construct lacking a functional gene coding for a factor required to initiate replication from said origin of replication, the method comprising (a) transforming bacterial cells with a parental plasmid vector which comprises a first origin of replication and a second origin of replication in the same orientation as the first origin of replication, which first and second origins of replication are sufficiently similar to be functional with the same replication factor, the first and second origins of replication dividing the vector into two parts, (i) a first part comprising the first origin of replication and a gene encoding a replication factor required for plasmid replication from said first and second origin of replication, and (ii) a second part comprising the second origin of replication, a DNA sequence of interest, and a DNA sequence which is homologous with a region of the genome of a cell intended for introduction of the vector, and (b) culturing the transformed cells under selective conditions, replication of the parental plasmid vector giving rise to the formation of a first progeny vector comprising the first origin of replication and a functional gene encoding a replication factor required for plasmid replication from said first and second origin of replication, and a second progeny vector comprising the second origin of replication but lacking a functional gene encoding a replication factor, as well as comprising a DNA sequence of interest, and a DNA sequence which is homologous with a region of the genome of the cell, continued culturing of the transformed cells under selective conditions resulting in the integration of said second progeny vector into the bacterial genome by homologous recombination and loss of the first progeny vector as well as the parental vector from the cells.

2. A method according to claim 1, wherein the second origin of replication is derived from the same plasmid as the first origin of replication.

3. A method according to claim 1, wherein a gene encoding the replication factor associated with the second origin of replication of the second progeny vector of step(b) has been deleted.

4. A method according to claim 1, wherein a gene encoding the replication factor associated with the second origin of replication of the second progeny vector of step(b) has been modified.

5. A method according to claim 4, wherein the gene encoding the replication factor has been modified by deletion, insertion or substitution of one or more nucleotides of the DNA sequence of the gene, or by deletion of transcriptional or translational start or stop signals.

6. A method according to claim 1, wherein the parental plasmid vector is one which is unable to replicate at increased temperatures which yet permit growth of the host cell, and wherein the bacterial cells are initially cultured at a temperature permitting plasmid replication and subsequently, after integration of the second progeny vector into the bacterial genome, cultured at a temperature which does not permit plasmid replication so that the first progeny vector as well as the parental vector are lost from the cells.

7. A method according to claim 1 in which the first and second origins of replication associated with the parental vector are each derived from a single-stranded DNA plasmid.

8. A method according to claim 7, wherein the second origin of replication is derived from the same single-strand DNA plasmid as the first origin of replication.

9. A method according to claim 1, wherein the bacterial cell is a cell of a gram-positive bacterium.

10. A method according to claim 9, wherein the gram-positive bacterium is a strain belonging to the genus Bacillus or Streptomyces.

11. A method according to claim 10, wherein the bacterium is a strain of *Bacillus licheniformis, Bacillus lentus, Bacillus brevis, Bacillus stearothermophilus, Bacillus alkalophilus, Bacillus amyloliquefaciens, Bacillus coagulans, Bacillus subtilis* or *Streptomyces lividans*.

12. A method of producing a bacterial cell which in its genome carries an integrated non-replicative DNA construct comprising (1) a DNA sequence of interest, (2) a DNA sequence which is homologous with a region of the genome of the cell, and (3) an origin of replication, the DNA construct lacking a functional gene coding for a factor required to initiate replication from said origin of replication, the method comprising (a) transforming bacterial cells with (i) a first DNA vector comprising a first origin of replication and a functional gene encoding a factor required for plasmid replication from said first origin of replication, and with (ii) a second DNA vector comprising a second origin of replication but lacking a functional gene encoding a factor required for plasmid replication from the second origin of replication, as well as comprising a DNA sequence of interest, and a DNA sequence which is homologous with a region of the genome of the cell, said first and second origins of replication being sufficiently similar to be functional with the same replication factor so that replication of the second DNA vector from the second origin of replication is initiated by the replication factor encoded by the gene present on the first DNA vector, and (b) culturing the resulting cells under selective conditions leading to integration of said second DNA vector into the bacterial genome by homologous recombination and loss of the first DNA vector.

13. A method according to claim 12, wherein the second origin of replication is derived from the same plasmid as the first origin of replication.

14. A method according to claim 12, wherein the second DNA vector has been deleted of the gene encoding the replication factor associated with the second origin of replication.

15. A method according to claim 14, wherein the gene encoding the replication factor associated with the second origin of replication has been modified by deletion, insertion or substitution of one or more nucleotides of the DNA sequence of the gene, or by deletion of transcriptional or translational start or stop signals.

16. A method according to claim 12, wherein the second DNA vector further comprises a selectable marker.

17. A method according to claim 12, wherein the first DNA vector comprises a first plus origin of replication from a single-strand DNA plasmid and a functional rep gene, and wherein the second DNA vector comprises a second plus origin of replication from a single-strand DNA plasmid but lacking a functional rep gene cognate to the second plus origin of replication, as well as comprising a DNA sequence of interest, and a DNA sequence which is homologous with a region of the genome of said cell.

18. A method according to claim 17, wherein the second plus origin of replication is derived from the same single-strand DNA plasmid as the first plus origin of replication.

19. A method according to claim 12, wherein the first DNA vector is one which is unable to replicate at increased temperatures which yet permit growth of the host cells, and wherein the bacterial cells are initially cultured at a temperature permitting plasmid replication and subsequently, after integration of the second DNA vector into the bacterial genome, cultured at a temperature which does not permit plasmid replication so that the first DNA vector is lost from the cells.

20. A method according to claim 12, which is a cell of a gram-positive bacterium.

21. A method according to claim 20, wherein the gram-positive bacterium is a strain belonging to the genus Bacillus or Streptomyces.

22. A method according to claim 21, wherein the bacterium is a strain of *Bacillus licheniformis, Bacillus lentus, Bacillus brevis, Bacillus stearothermophilus, Bacillus alkalophilus, Bacillus amyloliquefaciens, Bacillus coagulans, Bacillus subtilis* or *Streptomyces lividans*.

23. A bacterial cell obtainable according to the method of claim 1 or 12 which in its genome carries an integrated non-replicative DNA construct comprising (1) a DNA sequence of interest, (2) a DNA sequence which is homologous with a region of the genome of the cell, and (3) an origin of replication, wherein the DNA construct has been deleted of a gene coding for a factor required to initiate replication from said origin of replication or wherein the gene encoding the replication factor has been modified so as to encode an inactive replication factor.

24. A cell according to claim 23, wherein the DNA construct has been deleted of the gene encoding the replication factor.

25. A cell according to claim 23, wherein the gene encoding the replication factor has been modified so as to encode an inactive replication factor.

26. A cell according to claim 25, wherein said gene has been modified by deletion, insertion or substitution of one or more nucleotides of the DNA sequence of the gene, or by deletion of transcriptional or translational start or stop signals.

27. A cell according to claim 23, wherein the DNA construct comprises a DNA sequence of interest, a DNA sequence which is homologous to a region of the genome of the cell, and a plus origin of replication from a single-strand DNA plasmid, the DNA construct lacking a functional rep gene cognate to the plus origin of replication.

28. A cell according to claim 23, wherein the DNA construct additionally comprises a selectable marker.

29. A cell according to claim 23, which is a cell of a gram-positive bacterium.

30. A cell according to claim 29, wherein the gram-positive bacterium is a strain belonging to the genus Bacillus or Streptomyces.

31. A cell according to claim 30, wherein the bacterium is a strain of *Bacillus licheniformis, Bacillus lentus, Bacillus brevis, Bacillus stearothermophilus, Bacillus alkalophilus, Bacillus amyloliquefaciens, Bacillus coagulans, Bacillus subtilis* or *Streptomyces lividans*.

32. A process for producing a polypeptide of interest, comprising culturing a bacterial cell according to claim 23 containing an integrated DNA sequence which codes for said polypeptide under conditions conducive to the production of the polypeptide and recovering the resulting polypeptide from the culture.

33. A process according to claim 32, wherein the polypeptide is an enzyme.

34. A process according to claim 33, wherein the enzyme is a protease, amylase or lipase.

35. A parental plasmid vector which comprises a first origin of replication and a second origin of replication in the same orientation as the first origin of replication, which first and second origins of replication are sufficiently similar to be functional with the same replication factor(s), the first and second origins of replication dividing the vector into two parts, (i) a first part comprising the first origin of replication and one or more functional genes encoding the replication factor(s) required for plasmid replication from said first and second origin of replication, and (ii) a second part comprising the second origin of replication, a DNA sequence of interest, and a DNA sequence which is homologous with a region of the genome of a cell intended for introduction of the vector.

36. A plasmid vector according to claim 35, wherein the second origin of replication is derived from the same plasmid as the first origin of replication.

37. A plasmid vector according to claim 35, which has been deleted of the gene encoding the replication factor associated with the second origin of replication.

38. A plasmid vector according to claim 35, wherein the gene encoding the replication factor associated with the second origin of replication has been modified.

39. A plasmid vector according to claim 38, wherein the gene has been modified by deletion, insertion or substitution of one or more nucleotides of the DNA sequence of the gene, or by deletion of transcriptional or translational start or stop signals.

40. A plasmid vector according to claim 35 in which the first and second origins of replication associated with the parental vector are each derived from a single-stranded DNA plasmid.

41. A plasmid vector according to claim 40, wherein the second origin of replication is derived from the same single-strand DNA plasmid as the first origin of replication.

42. A plasmid vector according to claim 35, which further comprises a selectable marker.

43. A recombinant DNA vector comprising (1) a DNA sequence of interest, (2) a DNA sequence which is homologous with a region of the genome of the cell, and (3) an origin of replication, the DNA construct lacking a functional gene coding for a factor required to initiate replication from said origin of replication.

44. A vector according to claim 43, which has been deleted of the gene encoding the replication factor.

45. A vector according to claim 43, wherein the gene encoding the replication factor has been modified so as to encode an inactive replication factor.

46. A vector according to claim 45, wherein said gene has been modified by deletion, insertion or substitution of one or more nucleotides of the DNA sequence of the gene, or by deletion of transcriptional or translational start or stop signals.

47. A vector according to claim 43, comprising a DNA sequence of interest, a DNA sequence which is homologous with a region of the genome of a cell intended for introduction of the vector, and a plus origin of replication from a single-strand DNA plasmid, the vector lacking a functional rep gene associated with the plus origin.

48. A vector according to claim 43, which additionally comprises a selectable marker.

49. A bacterial cell which comprises a first DNA vector comprising an origin of replication and one or more functional genes encoding the factor(s) required for plasmid replication from said first origin of replication, and a second DNA vector according to claim 43.

* * * * *